(12) United States Patent
Hashizume et al.

(10) Patent No.: US 8,487,264 B2
(45) Date of Patent: Jul. 16, 2013

(54) RADIATION TOMOGRAPHY APPARATUS

(75) Inventors: Nobuya Hashizume, Kyoto (JP); Keishi Kitamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 353 days.

(21) Appl. No.: 13/056,240

(22) PCT Filed: Sep. 5, 2008

(86) PCT No.: PCT/JP2008/066085
§ 371 (c)(1),
(2), (4) Date: Jan. 27, 2011

(87) PCT Pub. No.: WO2010/013356
PCT Pub. Date: Feb. 4, 2010

(65) Prior Publication Data
US 2011/0127436 A1     Jun. 2, 2011

(30) Foreign Application Priority Data
Jul. 31, 2008   (JP) ................................. 2008-198415

(51) Int. Cl.
   *G01T 1/20*   (2006.01)
(52) U.S. Cl.
   USPC ............ 250/363.04; 250/370.09; 250/370.11
(58) Field of Classification Search
   USPC ............... 250/363.04, 363.01–363.09, 363.1,
           250/370.01–370.09, 370.1, 370.11–370.15;
           382/132
   See application file for complete search history.

(56) References Cited

U.S. PATENT DOCUMENTS

| | | | | |
|---|---|---|---|---|
| 4,008,400 | A * | 2/1977 | Brunnett et al. | 378/4 |
| 4,575,868 | A * | 3/1986 | Ueda et al. | 378/4 |
| 5,802,134 | A * | 9/1998 | Larson et al. | 378/4 |
| 5,881,122 | A * | 3/1999 | Crawford et al. | 378/4 |
| 6,255,655 | B1 * | 7/2001 | Mc Croskey et al. | 250/363.03 |
| 7,218,701 | B2 * | 5/2007 | Ueno et al. | 378/19 |
| 7,262,415 | B2 * | 8/2007 | Crosetto | 250/363.05 |
| 7,507,968 | B2 * | 3/2009 | Wollenweber et al. | 250/363.07 |
| 2002/0148970 | A1 * | 10/2002 | Wong et al. | 250/394 |
| 2004/0195512 | A1 * | 10/2004 | Crosetto | 250/363.04 |
| 2006/0173302 | A1 * | 8/2006 | Conwell | 600/436 |
| 2006/0273250 | A1 * | 12/2006 | Ishitsu et al. | 250/252.1 |

(Continued)

OTHER PUBLICATIONS

Ferreira, N.C. et al., "Influence of Malfunctioning Block Detectors on the Calculation of Single Detector Efficiencies in PET", IEEE Transactions on Nuclear Science, 1999, vol. 46, No. 4, pp. 1062-1069.

*Primary Examiner* — David Porta
*Assistant Examiner* — Taeho Jo
(74) *Attorney, Agent, or Firm* — Cheng Law Group, PLLC

(57) ABSTRACT

A detector ring of radiation tomography apparatus according to this invention has a fracture portion having no scintillation counter crystal arranged therein. Moreover, the radiation tomography apparatus according to this invention includes a correlated data complementation section. The correlated data complementation section forms correlated data when assuming that a first scintillation counter crystal actually provided in the detector ring is in the fracture portion, and additionally stores it to a correlated data storing section, thereby complementing correlated data in the fracture portion. As noted above, the correlated data complementation section obtains positional information under assumption that the scintillation counter crystals are in the fracture portion and a corresponding number of coincident events. Consequently, this invention may realize acquisition of faithful detecting efficiencies in the scintillation counter crystals. Therefore, the radiation tomography apparatus may be provided that allows creation of radiological images suitable for diagnosis.

20 Claims, 23 Drawing Sheets

U.S. PATENT DOCUMENTS

2008/0042067 A1* 2/2008 Rousso et al. ........... 250/363.04
2008/0137806 A1* 6/2008 Chang ............................ 378/17
2009/0032716 A1* 2/2009 Wieczorek et al. ...... 250/363.04
2011/0096897 A1* 4/2011 Tonami et al. .................. 378/21

* cited by examiner

Fig. 8
(a)
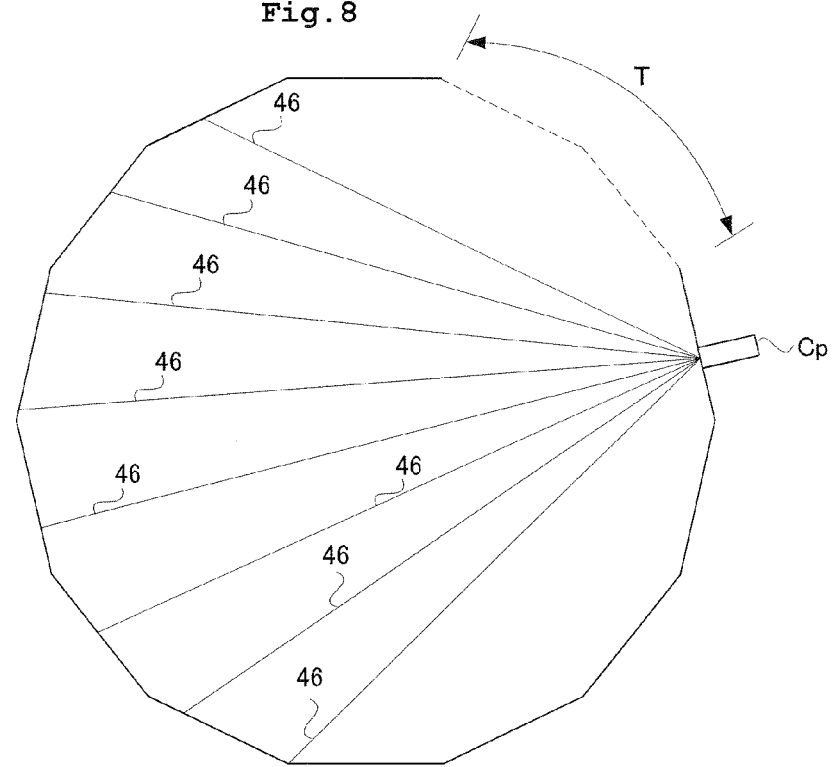
(b)
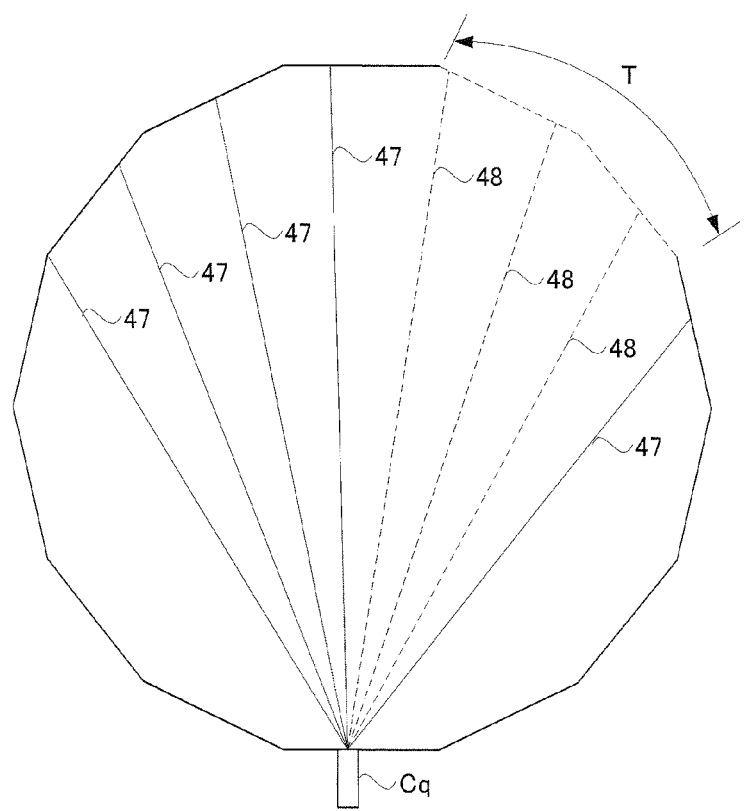

(a) Fig.10
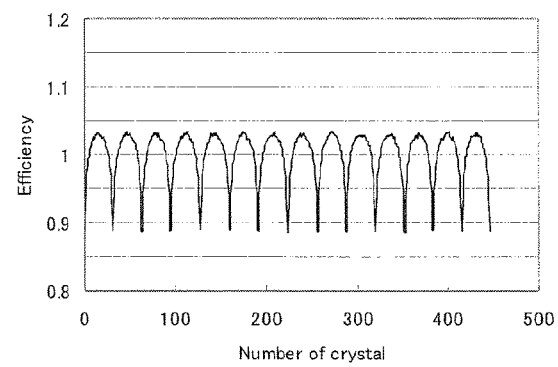
(b)
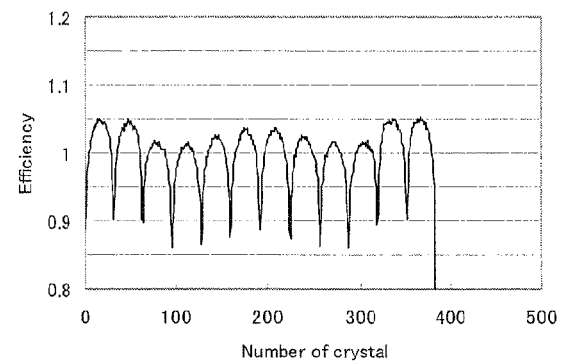
(c)
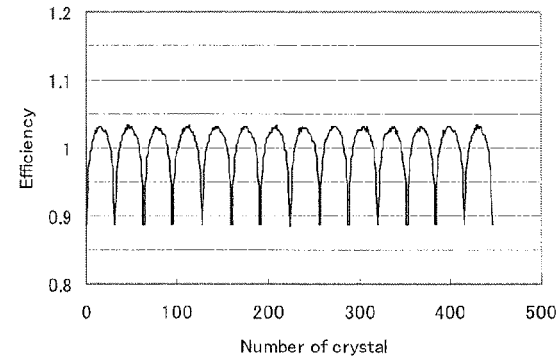
(d)
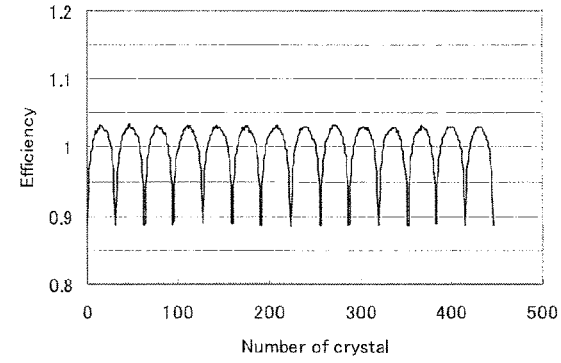

Fig. 11
(a)
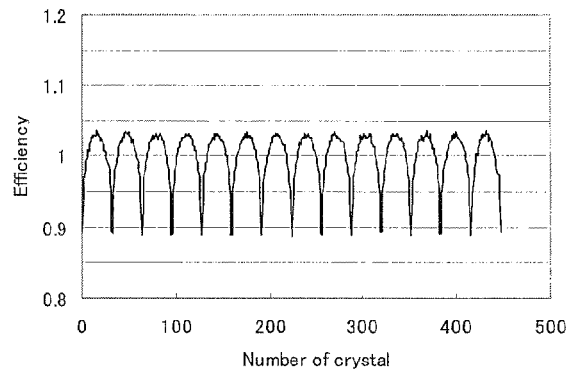
(b)
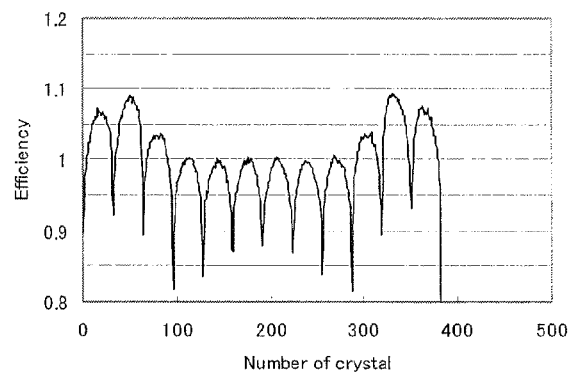
(c)
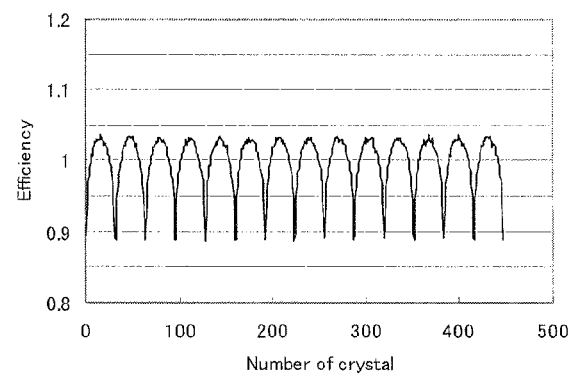
(d)
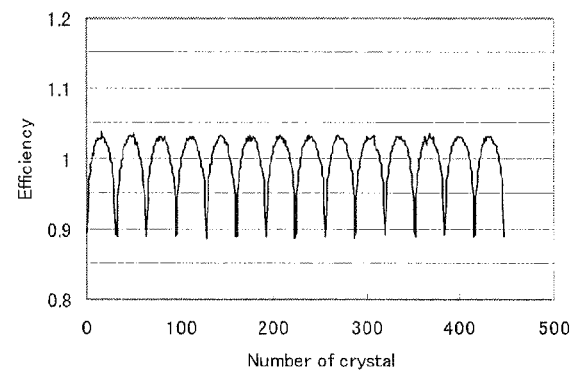

Fig. 12
(a) 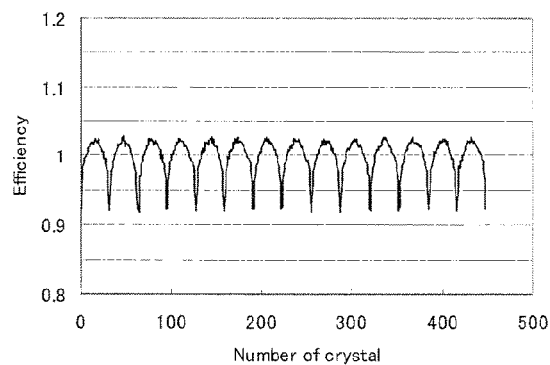
(b) 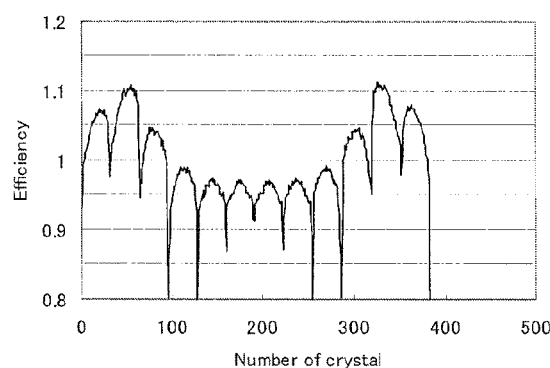
(c) 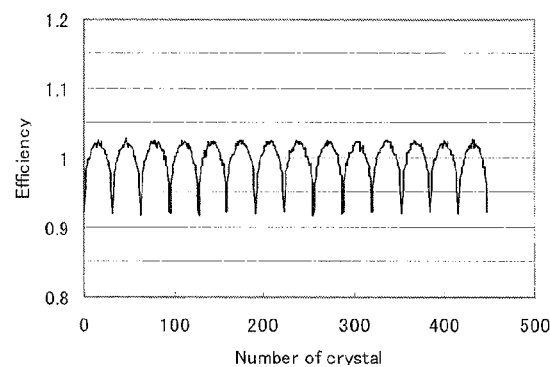
(d) 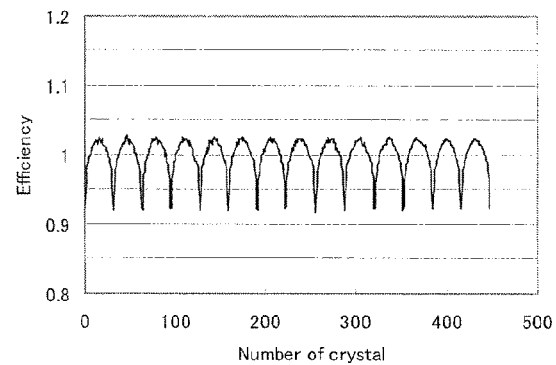

(a) Fig.13
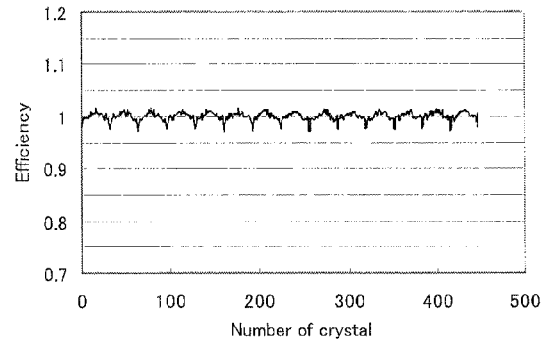
(b)
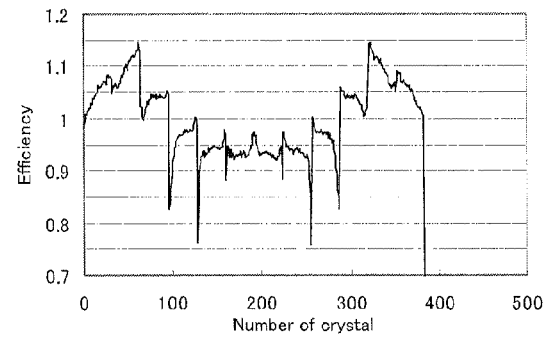
(c)
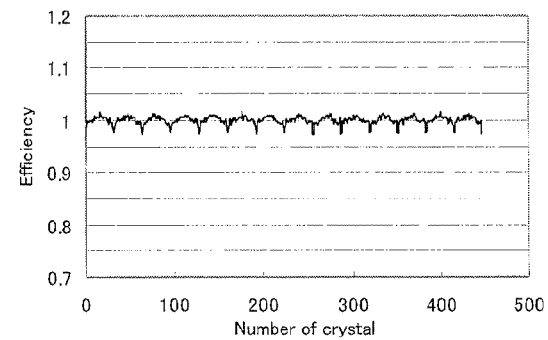
(d)
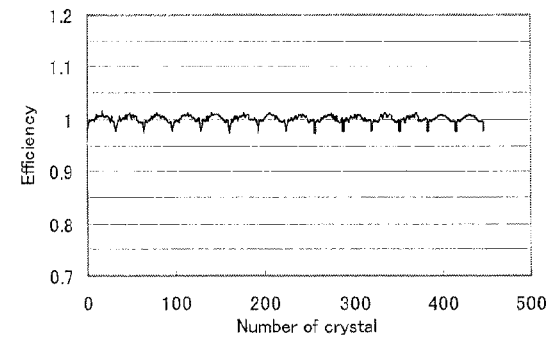

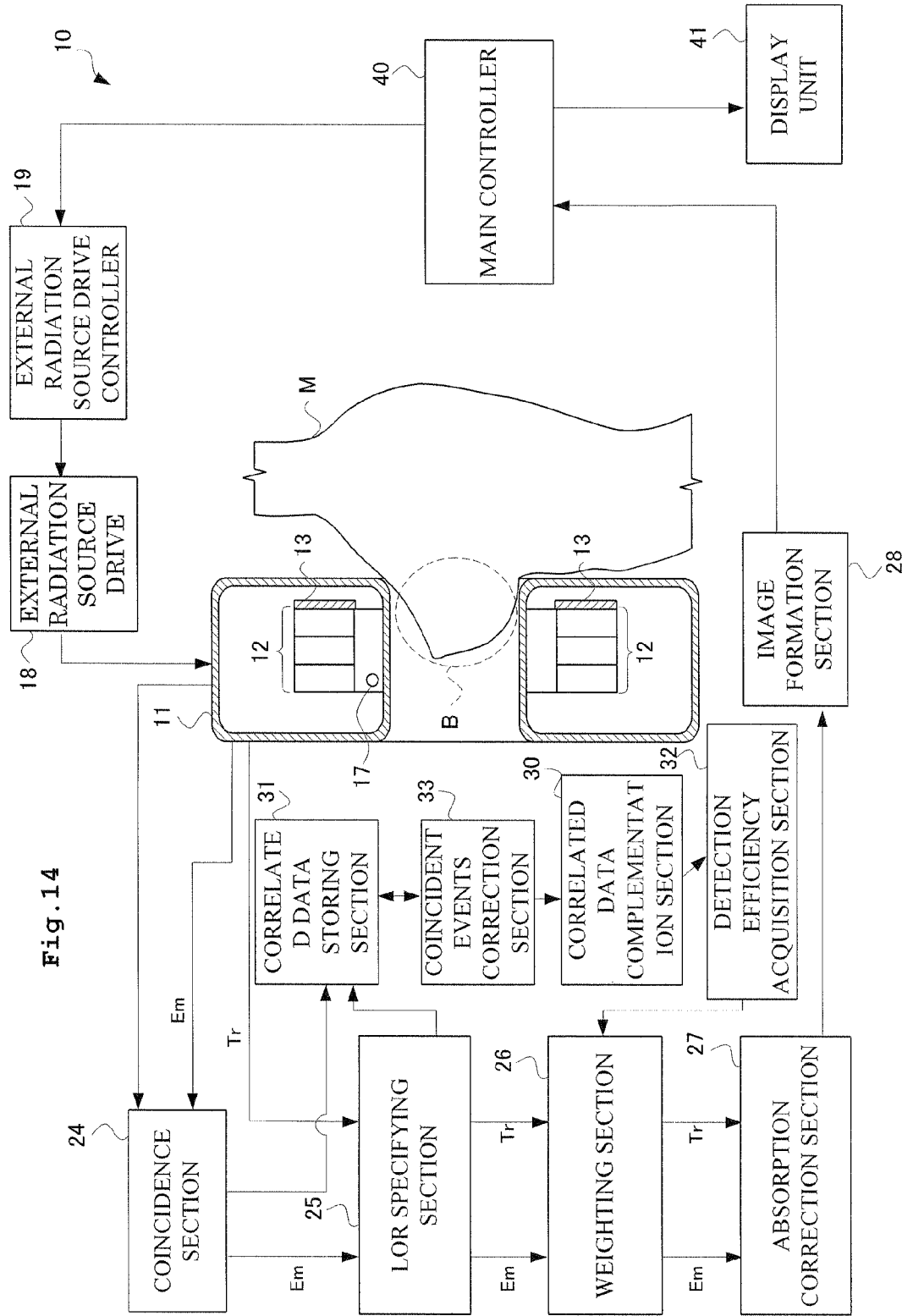

Fig.21
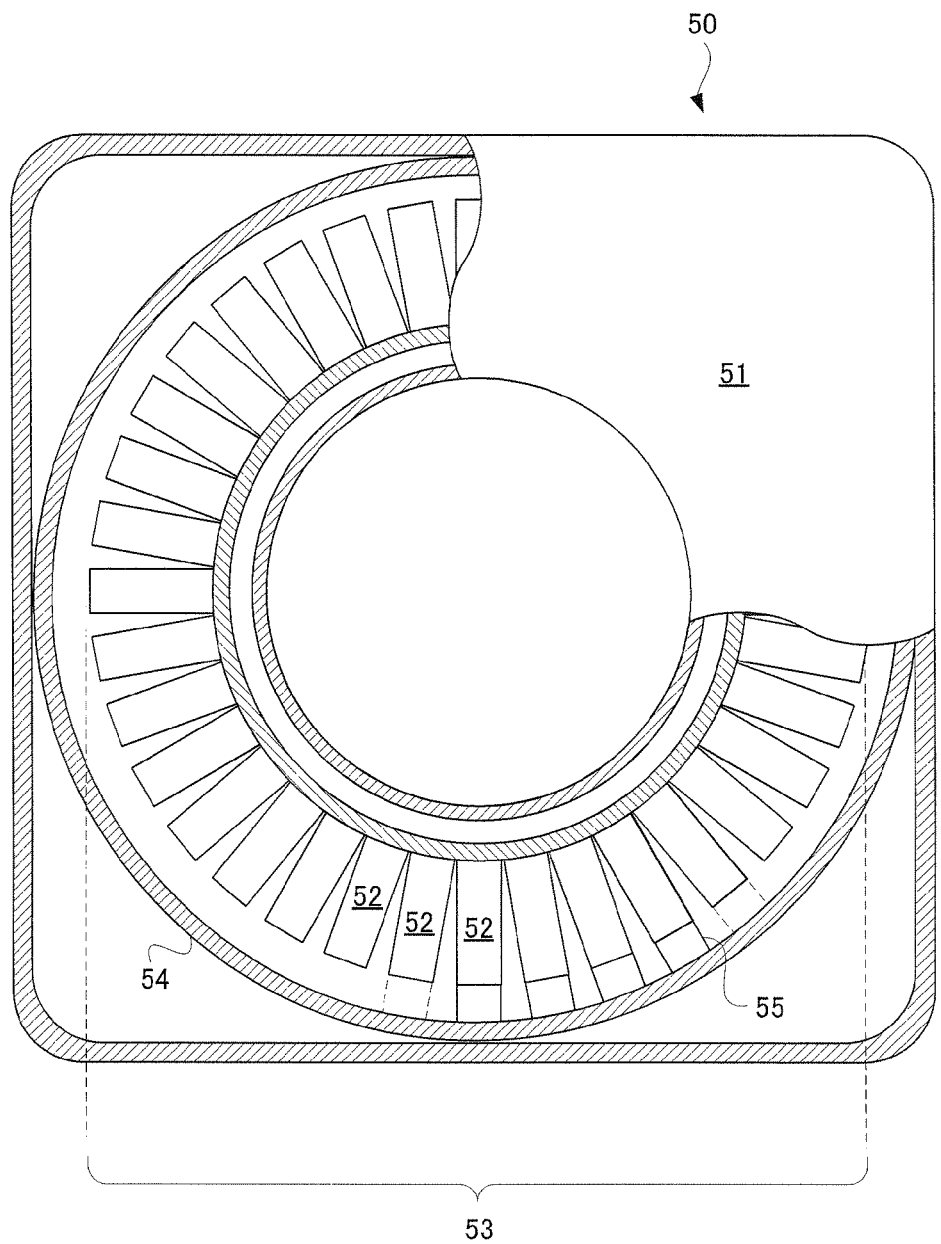
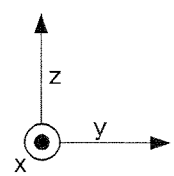

Fig.23
(a)
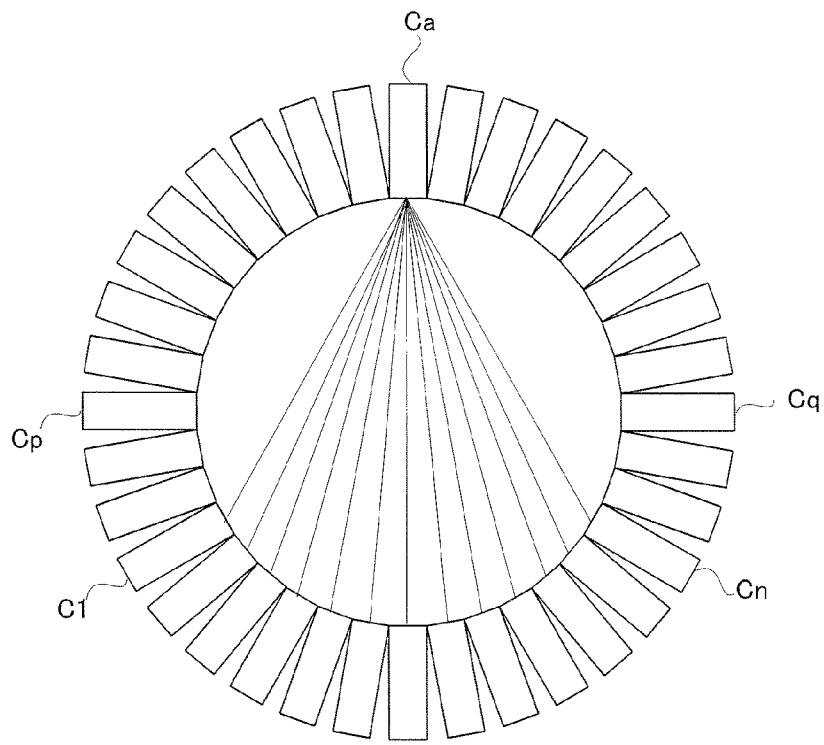
(b)
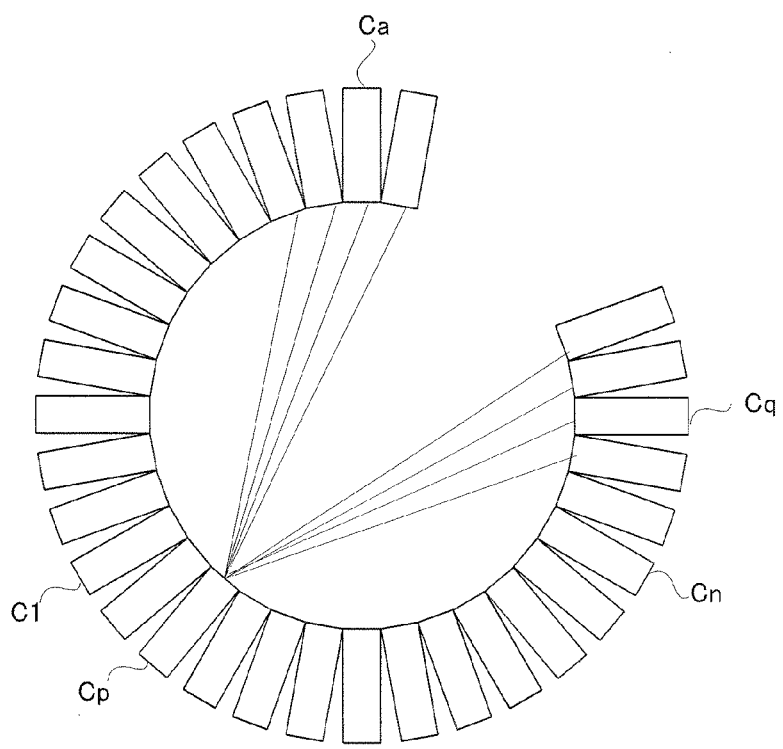

RADIATION TOMOGRAPHY APPARATUS

TECHNICAL FIELD

This invention relates to radiation tomography apparatus that images radiation. Particularly, this invention relates to radiation tomography apparatus having block radiation detectors arranged in a ring shape.

BACKGROUND ART

In medical fields, radiation emission computed tomography (ECT: Emission Computed Tomography) apparatus is used that detects an annihilation radiation pair (for example, gamma rays) emitted from radiopharmaceutical that is administered to a subject and is localized to a site of interest for obtaining sectional images of the site of interest in the subject showing radiopharmaceutical distributions. Typical ECT apparatus includes, for example, a PET (Positron Emission Tomography) device and an SPECT (Single Photon Emission Computed Tomography) device.

A PET device will be described by way of example. The PET device has a detector ring with block radiation detectors arranged in a ring shape. The detector ring is provided for surrounding a subject, and allows detection of radiation that is transmitted through the subject.

Such radiation detector arranged in the detector ring of the PET device is often equipped that allows position discrimination in a depth direction of a scintillator provided in the radiation detector for enhanced resolution. First, description will be given of a configuration of a conventional PET device. As shown in FIG. 21, a conventional PET device 50 includes a gantry 51 with an introducing hole that introduces a subject, a detector ring 53 having block radiation detectors 52 for detecting radiation being arranged inside the gantry 51 so as to surround the introducing hole, and a support member 54 provided so as to surround the detector ring 53. Each of the radiation detectors 52 has a bleeder unit 55 with a bleeder circuit in a position between the support member 54 and thereof for connecting the support member 54 and the radiation detector 52. The bleeder unit 55 is coupled to a light detector 62, mentioned later, in the radiation detector 52.

Next, description will be given of a construction of the radiation detector 52. As shown in FIG. 22, the conventional radiation detector 52 includes a scintillator 61 that converts radiation into fluorescence, and a photomultiplier tube (hereinafter referred to as a light detector) 62 that detects fluorescence. The scintillator 61 has scintillation counter crystals 63 of rectangular solid that are arranged in a three-dimensional array. The light detector 62 allows discrimination about which scintillation counter crystal 63 emits fluorescence. That is, the radiation detector 52 may discriminate an incidence position of radiation in the scintillator 61.

The PET device 50 obtains images on a site of interest of the subject through detection of annihilation radiation-pairs. Specifically, the annihilation radiation-pairs having opposite directions are emitted from radiopharmaceutical that is administered to the subject introduced into the PET device 50. Two different scintillators 61 detect the annihilation radiation-pair. Radiation detection efficiency, however, is not necessarily uniform throughout the scintillators 61. Lack of uniformity of detection efficiencies leads to reduced visibility of a radiological image.

Thus, a conventional PET device 50 uses a fan-sum method for measuring in advance lack of uniformity of radiation detection efficiencies in each scintillator 61. Then, one pair of scintillators 61 detects the annihilation radiation-pair emitted from the radiopharmaceutical administered to the subject. At this time, the lack of uniformity of radiation detection efficiencies in each scintillator 61 is cancelled with reference to the acquired lack of uniformity of detection efficiencies acquired in advance. Such configuration is described, for example, in Non-Patent Literature 1.

[Non-Patent Literature 1]
IEEE TRANSACTIONS ON NUCLEAR SCIENCE (the United States), VOL. 46, NO. 4, AUGUST 1999, Page 1062-1069

DISCLOSURE OF THE INVENTION

Summary of the Invention

According to the conventional configuration, however, the fan-sum method may be used only for a detector ring having radiation detectors arranged in a ring shape. That is, the fan-sum method is not simply applicable to a PET-Mammo device for breast inspections having radiation detectors arranged in a C-shape. Accordingly, the PET-Mammo device for breast inspections cannot satisfactorily measure lack of uniformity of radiation detection efficiencies in each scintillator 61.

Now, brief description will be given of the conventional fan-sum method. FIG. 23 conceptually shows the conventional fan-sum method. Scintillation counter crystals C1 to Cn on an opposite side to a scintillation counter crystal Ca are used for obtaining the radiation detection efficiency in the scintillation counter crystal Ca. Specifically, a radiation detection efficiency in a scintillation counter crystal Ca is obtained by use of correlated data acquired when one of the annihilation radiation-pair enters into the scintillation counter crystal Ca and the other of the annihilation radiation-pair enters into any of the scintillation counter crystals C1 to Cn, as shown in FIG. 23. Correlated data on radiation due to other than combination of the above scintillation counter crystals is not used for obtaining the radiation detection efficiency in the scintillation counter crystal Ca. The scintillation counter crystal Ca is connected to each of the scintillation counter crystals C1 to Cn with lines to form a fan shape. This is called a fan region.

Calculation is made of the detection efficiency in the scintillation counter crystal Ca. Likewise, a radiation detection efficiency is subsequently to be calculated in a scintillation counter crystal adjacent to the scintillation counter crystal Ca. As above, a radiation detection efficiency in every scintillation counter crystal may be obtained. Accordingly, lack of uniformity of radiation detection efficiencies is found in each scintillation counter crystal.

In FIG. 23(a), the scintillation counter crystals Cp and scintillation counter crystal Cq are opposite to each other. In addition, a fan region with the centered scintillation counter crystal Cp has the same shape as that with the centered scintillation counter crystal Cq. In other words, these fan regions have the same shape as the scintillation counter crystal Ca. That is because the scintillation counter crystals are annularly arranged. All scintillation counter crystals have rotational symmetry. Consequently, the fan-sum method ensures uniformity in measurement condition on detection efficiency in each scintillation counter crystal.

On the other hand, the PET-Mammo device for breast inspections has radiation detectors arranged in a C-shape. The site of interest of the subject is necessarily introduced into an opening of the gantry 51 more deeply for obtaining a radiological image suitable for diagnosis. Thus, it is more desirable to contact an arm of the subject to the gantry 51. For this purpose, the gantry 51 has a C-shape. Moreover, a detector ring 12 also has a shape following the gantry 51, and thus cannot have radiation detectors arranged annularly. As a result, the PET-Mammo device has the radiation detectors arranged in a C-shape.

Herein in FIG. 23(b), the scintillation counter crystals Cp and Cq are opposite to each other. A fan region with the centered scintillation counter crystal Cp does not have the same shape as that with the centered scintillation counter crystal Cq. That is because the scintillation counter crystals are arranged with different rotational symmetry properties due to C-shape arrangement of the radiation detectors.

Calculation of radiation detection efficiency in the scintillation counter crystal is performed through the fan-sum method for determining lack of uniformity of radiation detection efficiencies in each scintillation counter crystal. Consequently, where the fan region with the centered scintillation counter crystal Cp does not have the same shape as that with the centered scintillation counter crystal Cq, it is represented that lack of uniformity of radiation detection efficiencies in each scintillation counter crystal cannot be determined accurately. That is because the scintillation counter crystals Cp and Cq differ from each other in fan region for calculating the radiation detection efficiency.

This invention has been made regarding the state of the art noted above, and its object is to provide radiation tomography apparatus that allows acquisition of lack of uniformity of radiation detection efficiencies in each scintillation counter crystal upon calculation of detection efficiency in the scintillation counter crystals with ensured measurement condition thereof even when radiation detectors are arranged in a C-shape.

Means for Solving the Problem

This invention is constituted as stated below to achieve the above object. Radiation tomography apparatus includes a detector ring having radiation detecting elements for detecting radiation arranged in an arc shape; a coincidence device for counting a number of coincident events as a frequency where a first radiation detecting element and a second radiation detecting element coincidentally detect radiation; a position specifying device for outputting positional information as a line connecting the first radiation detecting element and the second radiation detecting element; and a correlated data storing device for storing correlated data having the number of coincident events and corresponding positional information correlated therewith. The detector ring has an array portion where radiation detecting elements for detecting radiation are arranged, and a fracture portion where no radiation detecting element is arranged. The apparatus further includes a correlated data complementation device for complementing correlated data on the fracture portion by calculating the number of coincident events and positional information corresponding thereto based on the correlated data under assumption that the first radiation detecting element is in the fracture portion for storing the number of coincident events and the positional information to the correlated data complementation device in addition; a detection efficiency acquisition device for acquiring a radiation detection efficiency in each radiation detecting element arranged in the detector ring by use of the correlated data and the correlated data through complementation; and a correction device for correcting a radiological image in accordance with the radiation detection efficiency.

[Operation and Effect]

The detector ring according to the configuration of this invention has the fracture portion having no radiation detecting element arranged. That is, the radiation detecting elements that constitute the detector ring are arranged with different rotational symmetry properties. When the fan-sum method is conventionally applied to such configuration, the detection efficiency is calculated under different conditions. That is because the radiation detecting elements differ from one another in shape of the fan region for the fan-sum method. Accordingly, the calculated detection efficiency has no faithful reproducibility of the actual detection efficiency of the detecting element. However, this invention includes the correlated data complementation device. The correlated data complementation device complements the correlated data on the fracture portion by formation of correlated data under assumption that the first radiation detecting element that is actually in the detector ring is in the fracture portion for storing the correlated data to the correlated data complementation device in addition. As above, the correlated data complementation device may obtain positional information and the number of coincident events corresponding thereto under assumption that the radiation detecting element is arranged in the fracture portion. Upon calculation of the detection efficiency with the fan-sum method under such state, the radiation detecting elements have a same shape of the fan region for the fan-sum method. That is because complementation is made of the positional information that is not actually measurable due to the fracture portion and the number of coincidence evens corresponding thereto (correlated data). Accordingly, the calculated radiation detection efficiency according to this invention has more faithful reproducibility of the actual detection efficiency. Weighting processing of the radiological image with such detection efficiency may ensure positive removal of lack of uniformity of radiation detection efficiencies in each of the radiation detecting elements superimposed in the radiological image. According to this invention, the radiation tomography apparatus may be provided that allows creation of radiological images suitable for diagnosis.

The foregoing correlated data complementation device duplicates the correlated data stored with the correlated data storing device and assumes that the duplication is counted in the fracture portion, thereby determining and complementing the number of coincident events and the positional information corresponding thereto under assumption that the first radiation detecting element is in the fracture portion. Such configuration is more desirable.

[Operation and Effect]

According to the foregoing configuration, the complementation as noted above is performed by duplicating the correlated data stored with the correlated data storing device and assumes that the duplication is counted in the fracture portion. The correlated data is used that has already been stored in the correlated data storing device. The correlated data on the fracture portion may positively be complemented.

Moreover, the foregoing correlated data complementation device performs complementation of the number of coincident events and the positional information corresponding thereto in the fracture portion by virtually rotating the first and second radiation detecting elements while maintaining a relative position therebetween to assume that the first radiation detecting element is in the fracture portion. Such configuration is more desirable.

[Operation and Effect]

The above configuration further embodies a method of complementing the correlated data. In the foregoing configuration, the first and second radiation detecting elements belonging to the detector ring rotate virtually while maintaining a relative position therebetween to assume that the first radiation detecting element is in the fracture portion. That is, the correlated data complementation device may readily complete the complementation through assumption that the number of coincident events actually measured with the first and second radiation detecting elements belonging to the detector ring is the number of coincident events in the fracture portion.

Moreover, the foregoing correlated data complementation device may complement the number of coincident events under assumption that the first radiation detecting element is in the fracture portion through average of two or more numbers of coincident events, and assumption of the average to be counted in the fracture portion.

[Operation and Effect]

The above configuration also embodies the method of complementing the correlated data. The correlated data complementation device performs complementation through average of two or more numbers of coincident events and assumption of the average to be counted in the fracture portion. In the foregoing configuration, the correlated data in the fractured portion is complemented not in accordance with a single piece of correlated data but in accordance with two or more pieces of correlated data. Consequently, more positive complementation may be realized.

The foregoing correlated data complementation device may perform complementation of the number of coincident events in the fracture portion as follows. That is, the first and second radiation detecting elements virtually rotate while the relative position therebetween is maintained. A pair of radiation detecting elements of rotational symmetry is collected as a pair of radiation detecting elements having rotational symmetry in positional relationship of the first and second radiation detecting elements for averaging a number of coincident events corresponding to the pair of radiation detecting elements of rotational symmetry. The average thereof is to be as the number of coincident events under assumption that the first radiation detecting element is in the fracture portion.

[Operation and Effect]

The above configuration embodies complementation of the correlated data in the fracture portion with two or more pieces of correlated data. Specifically, the first and second radiation detecting elements virtually rotate while the relative position therebetween is maintained, whereby the radiation detecting elements is collected. The number of coincident events in the pair of radiation detecting elements of rotational symmetry is considered equal to that in the pair of the first and second radiation detecting elements of rotational symmetry. That is because the pairs of the radiation detecting elements are same in its positional relationship. The number of coincident events suitable for complementation of correlated data in the fracture portion may be surely determined through averages of the number of coincident events in such pair of radiation detecting elements of rotational symmetry.

[Operation and Effect]

According to the foregoing configuration, the detection efficiency in the radiation detecting elements arranged in an array portion may be calculated more faithfully. Specifically, the detection efficiency acquisition device updates the radiation detection efficiency again based on the detection efficiency in the radiation detecting element once calculated. Consequently, the resultant detection efficiency approaches the actual detection efficiency.

The foregoing radiation detecting elements are arranged at least in an arc shape along a circle or polygon to form a unit detector ring having the radiation detecting elements arranged in a row. Two or more unit detector rings are stacked to form a detector ring. Such configuration is more desirable.

[Operation and Effect]

The foregoing configuration may provide radiation tomography apparatus having enhanced sensitivity. Specifically, the above configuration includes two or more unit detector rings. Consequently, more annihilation radiation-pairs may be observed in the subject in the radiation tomography apparatus. Therefore, the foregoing configuration may provide radiation tomography apparatus having enhanced sensitivity.

The above detector ring is formed of stacked unit detector rings each having detecting elements arranged in an arc shape. The correlated data complementation device complements a number of coincident events in the fracture portion by correcting the number of coincident events acquired from the radiation detecting elements constituting the detector ring and averaging them for determining an average of the number of coincident events, and by assuming it to be counted in the fracture portion. The detection efficiency acquisition device once sets a detection efficiency of the radiation detecting elements arranged in the array portion to be a predetermined value, and sets a detection efficiency of the radiation detecting elements assumed to be in the fracture portion to be a predetermined value for calculating a detection efficiency of the radiation detecting elements based on the corrected number of coincident events and the average of the number of coincident events. The detector efficiency acquisition device acquires again a detection efficiency of the radiation detecting elements arranged in the array portion based on the acquired detection efficiency of the radiation detecting elements and the detection efficiency of the radiation element assumed to be in the fracture portion. Here, let the number of coincident events assumed to be counted in the fracture portion be one that is obtained by multiplying the average of the number of coincident events calculated firstly by the detection efficiency of the radiation detecting elements calculated through previous calculation. The detection efficiency of the radiation detecting elements assumed to be in the fracture portion may be constant at a predetermined value.

The foregoing detector ring may also have two or more fracture portions spaced away from each other.

[Operation and Effect]

The foregoing configuration may provide various types of radiation tomography apparatus. The two or more fracture portions away from each other are namely two or more array portions divided with the fracture portions. Such configuration is often adopted in radiation tomography apparatus. Such configuration may calculate a detection efficiency of each the radiation detection element faithfully.

Effect of the Invention

The detector ring in this invention has a fracture portion having no radiation detecting element arranged therein. Moreover, this invention includes the correlated data complementation device. The correlated data complementation device forms correlated data when assuming that the first radiation detecting element actually provided in the detector ring is in the fracture portion, and additionally stores it to the correlated data storing device, thereby complementing correlated data in the fracture portion. As noted above, the correlated data complementation device obtains positional information under assumption that the radiation detecting elements are in the fracture portion and the corresponding number of coincident events.

Upon calculation of the detection efficiency with such configuration by use of the fan-sum method, the radiation detector elements may achieve the fan regions having a uniform shape for the fan-sum method. That is because complementation has been performed of the positional information that is not actually measurable due to the fracture portion and of the number of coincident events corresponding thereto (correlated data). Weighting processing of the radiological image with such detection efficiency may ensure positive removal of lack of uniformity of radiation detection efficiencies in each the radiation detecting element superimposed in the radiological image. According to this invention, the radiation tomography apparatus may be provided that allows creation of radiological images suitable for diagnosis.

According to the foregoing configuration, the complementation noted above may be performed by duplicating the correlated data stored with the data storing device and assumes that the duplication is counted in the fracture portion. According to the foregoing configuration, the correlated data is used that has already been stored in the data storing device. Consequently, the correlated data on the fracture portion may positively be complemented.

BRIEF DESCRIPTION OF THE DRAWINGS

FIG. 8 is a conceptual view showing operations of a detecting efficiency acquisition section according to Embodiment 1.

FIGS. 10 to 13 are simulation results each showing effects on complementation according to Embodiments 1 and 2.

FIG. 14 is a functional block diagram showing a configuration of radiation tomography apparatus according to Embodiment 3.

FIG. 21 is a sectional cut-away view showing a configuration of conventional radiation tomography apparatus.

FIG. 23 is a conceptual view showing a conventional fan-sum method.

DESCRIPTION OF REFERENCES

C scintillation counter crystal (radiation detecting element)
S array portion
T fracture portion
12 detector ring
12a unit detector ring
24 coincidence unit (coincidence device)
26 LOR specifying section (position specifying device)
30 correlated data complementation section (correlated data complementation device)
31 correlated data storing section (correlated data storing device)
32 detection efficiency acquisition section (detection efficiency acquisition device)

BEST MODE FOR CARRYING OUT THE INVENTION

Each embodiment of radiation tomography apparatus according to this invention will be described hereinafter with reference to the drawings.
Embodiment 1

Figure 1:
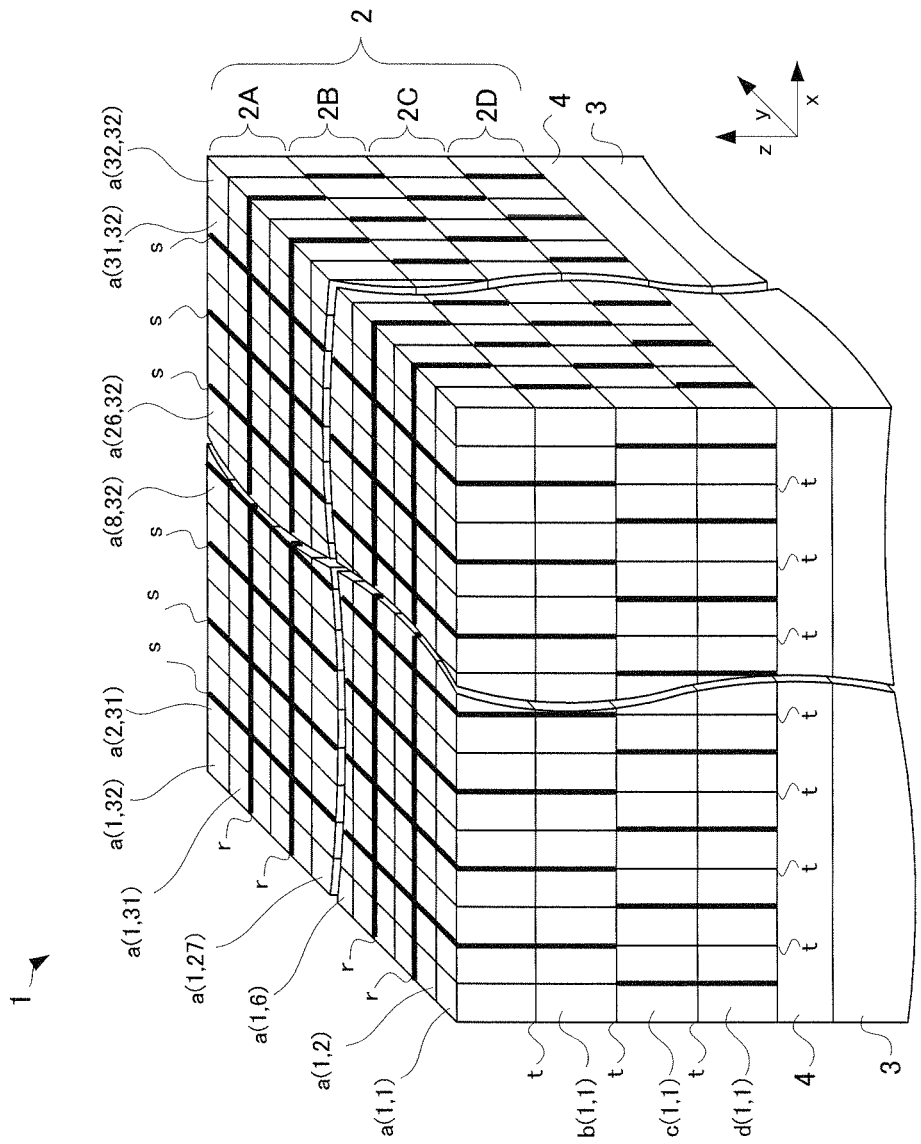
FIG. 1 is a perspective view of a radiation detector according to Embodiment 1.

Firstly, prior to explanation of the radiation tomography apparatus according to Embodiment 1, description will be given of a configuration of a radiation detector 1 according to Embodiment 1. FIG. 1 is a perspective view of the radiation detector according to Embodiment 1. As shown in FIG. 1, the radiation detector 1 according to Embodiment 1 includes a scintillator 2 that is formed of scintillation counter crystal layers each laminated in order of a scintillation counter crystal layer 2D, a scintillation counter crystal layer 2C, a scintillation counter crystal layer 2B, and a scintillation counter crystal layer 2A, in turn, in a z-direction, a photomultiplier tube (hereinafter referred to as a light detector) 3 having a function of position discrimination that is provided on an undersurface of the scintillator 2 for detecting fluorescence emitted from the scintillator 2, and a light guide 4 interposed between the scintillator 2 and the light detector 3. Consequently, each of the scintillation counter crystal layers is laminated in a direction toward the light detector 3. Here, the scintillation counter crystal layer 2A corresponds to an incident surface of radiation in the scintillator 2. Each of the scintillation counter crystal layers 2A, 2B, 2C, and 2D is optically coupled, and includes a transparent material t between each of the layers. A thermosetting resin composed of a silicone resin may be used for the transparent material t. The scintillation counter crystal layer 2A corresponds to a receiver of the gamma rays emitted from a radioactive source. The scintillation counter crystals in a block shape are arranged in a two-dimensional array with thirty-two numbers of the scintillation counter crystals in an x-direction and thirty-two numbers of the scintillation counter crystals in a y-direction relative to a scintillation counter crystal a (1, 1). That is, the scintillation counter crystals from a (1, 1) to a (1, 32) are arranged in the y-direction to form a scintillator crystal array. Thirty-two numbers of the scintillator crystal arrays are arranged in the x-direction to form a scintillation counter crystal layer 2A. Here, as for the scintillation counter crystal layers 2B, 2C, and 2D, thirty-two numbers of the scintillator counter crystals are also arranged in the x-direction and the y-direction in a matrix in a two-dimensional array relative to a scintillation counter crystal b (1, 1), c (1, 1), and d (1,1), respectively. In each of the scintillation counter crystal layers 2A, 2B, 2C, and 2D, the transparent material t is also provided between the scintillation counter crystals adjacent to each other. Consequently, each of the scintillation counter crystals is to be enclosed with the transparent material t. The transparent material t has a thickness around 25 μm. A gamma ray corresponds to radiation in this invention. A scintillation counter crystal corresponds to a radiation-detecting element of this invention.

First reflectors r that extend in the x-direction and second reflectors s that extend in the y-direction are provided in the scintillation counter crystal layers 2A, 2B, 2C, and 2D provided in the scintillator 2. Both reflectors r and s are inserted in a gap between the arranged scintillation counter crystals.

The scintillator 2 has scintillation counter crystals suitable for detection of gamma rays in a three-dimensional array. That is, the scintillation counter crystal is composed of Ce-doped $Lu_{2(1-x)}Y_{2x}SiO_5$ (hereinafter referred to as LYSO.) Each of the scintillation counter crystals is, for example, a rectangular solid having a length of 1.45 mm in the x-direction, a width of 1.45 mm in the y-direction, and a height of 4.5 mm regardless of the scintillation counter crystal layer. The scintillator 2 has four side end faces that are covered with a reflective film not shown. The light detector 3 is multi-anode type, and allows position discrimination of incident fluorescence in the x and y.

Figure 2:
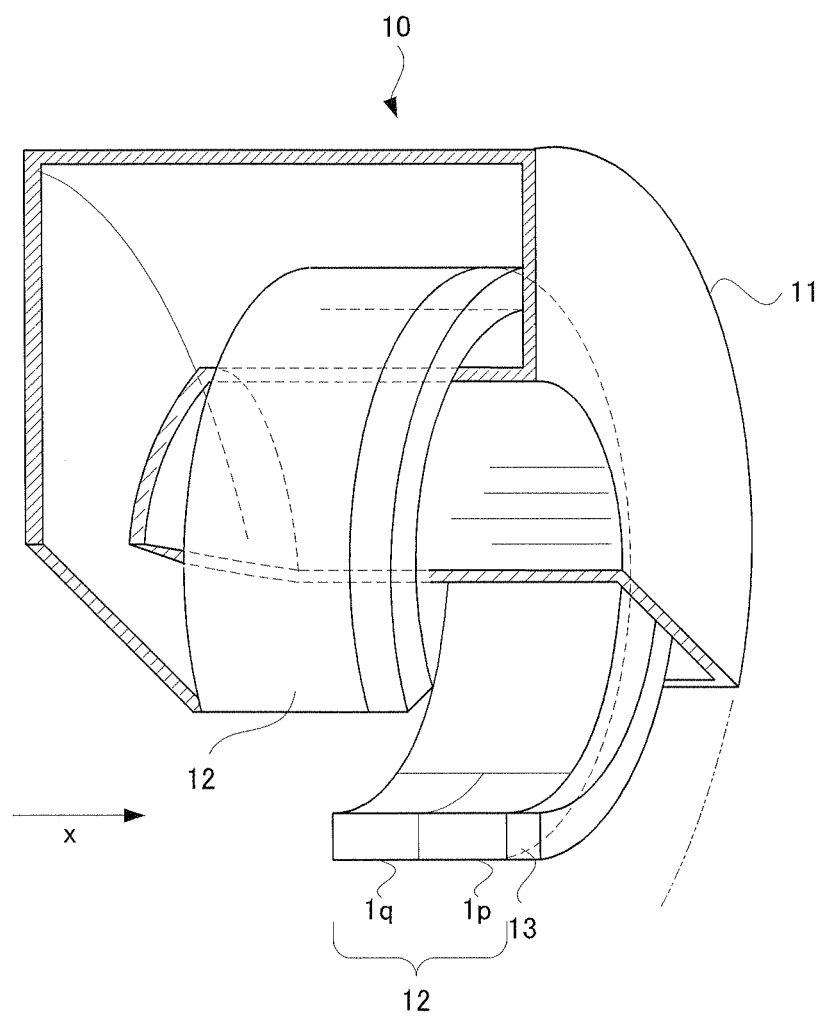
FIG. 2 is a sectional cut-away view showing a configuration of radiation tomography apparatus according to Embodiment 1.

Next, description will be given of a configuration of radiation tomography apparatus 10 according to Embodiment 1. FIG. 2 is a sectional cut-away view showing a configuration of the radiation tomography apparatus according to Embodiment 1. As shown in FIG. 2, the radiation tomography apparatus 10 according to Embodiment 1 has a gantry 11 having an opening for introducing a subject, and a detector ring 12 having radiation detectors arranged in a C-shape that is provided inside the gantry 11 so as to contain the opening of the gantry 11. The detector ring 12 has block radiation detectors 1p and 1q arranged in an arc shape. Gamma rays emitted from the subject enter into the detector ring 12. The detector ring 12 in the radiation tomography apparatus 10 determines intensity, an incidence period of time, and an incidence position of incident gamma rays. The detector ring corresponds to the group of radiation detectors in this invention. Moreover, the gantry 11 according to Embodiment 1 has an arc shape along the shape of the detector ring 12.

The radiation tomography apparatus 10 according to Embodiment 1 has a C-shaped shield 13 for preventing radiation derived from outside of the gantry 11 from entering into the detector ring 12. The shield 13 is provided as to cover one planar side end of the detector ring 12. Specifically, the shield 13 is provided on one side end of one planar pairs of the detector ring 12 that is adjacent to the opening for introducing the site of interest of the subject M in the radiation tomography apparatus 10. In other words, the shield 13 is provided such that the detector ring 12 extends in an axial direction. That is, the ring-shaped shield 13 divides a site other than the site B of interest of subject M outside the gantry 11 and the detector ring 12. The shield 13 is composed of Tungsten, etc.

Figure 3:
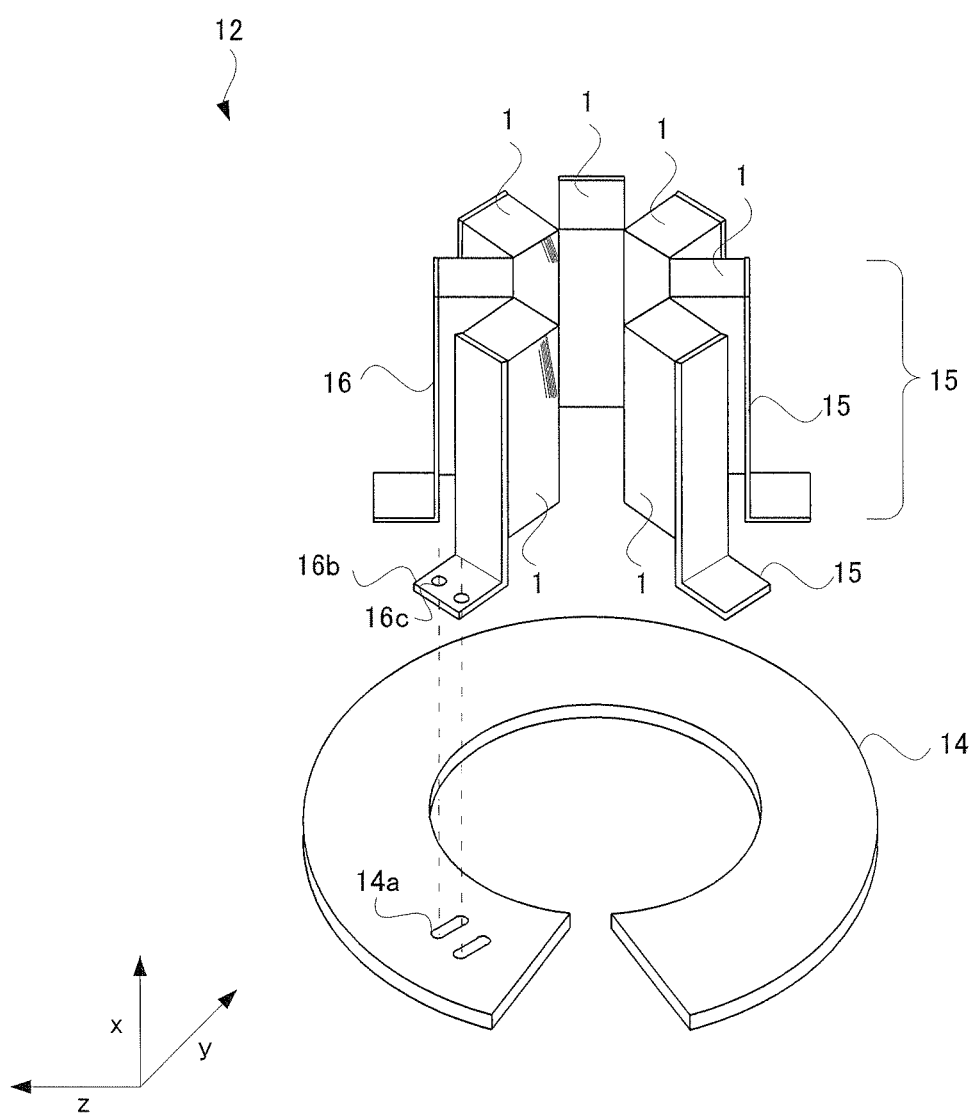
FIG. 3 is an exploded perspective view showing a configuration of a group of radiation detectors according to Embodiment 1.

Description will be given of a configuration of the detector ring 12. FIG. 3 is an exploded perspective view showing a configuration of a group of radiation detectors according to Embodiment 1. As shown in FIG. 3, the detector ring 12 has two or more detector units 15 arranged in an arc shape along a contour of a bottom plate 14 in a C-shape. The detector unit 15 has two radiation detectors 1 and an L-shaped holding member 16. The holding member 16 has a main plate 16a where the radiation detector 1 is held. In FIG. 3, seven detector units 15 are arranged in an arc shape following each side of an equilateral octagon. This is for simplification of the drawing. Actually, Embodiment 1 has a shape where twelve detector units 15 are arranged in an arc shape following each side of an equilateral tetradecagon.

Seen the detector ring 12 in the x-direction, the scintillators 2 provided in the detector unit 15 are arranged so as to face toward inside of the bottom plate 14. Accordingly, the scintillators 2 cover the inside of the detector ring 12. In addition, the detector unit 15 is fastened to the bottom plate 14 via a sub-plate 16b, mentioned later, with a bolt and a nut. Moreover, the sub-plate 16b has a hole 16c through which a bolt penetrates. The bottom plate 14 has a long hole 14a through which the bolt penetrates with respect to each detector unit 15. Embodiment 1 has a configuration where twelve detector units 15 are arranged along an arc portion. Specifically, twelve detector units 15 are arranged in an arc shape following each side of the equilateral tetradecagon.

Figure 4:
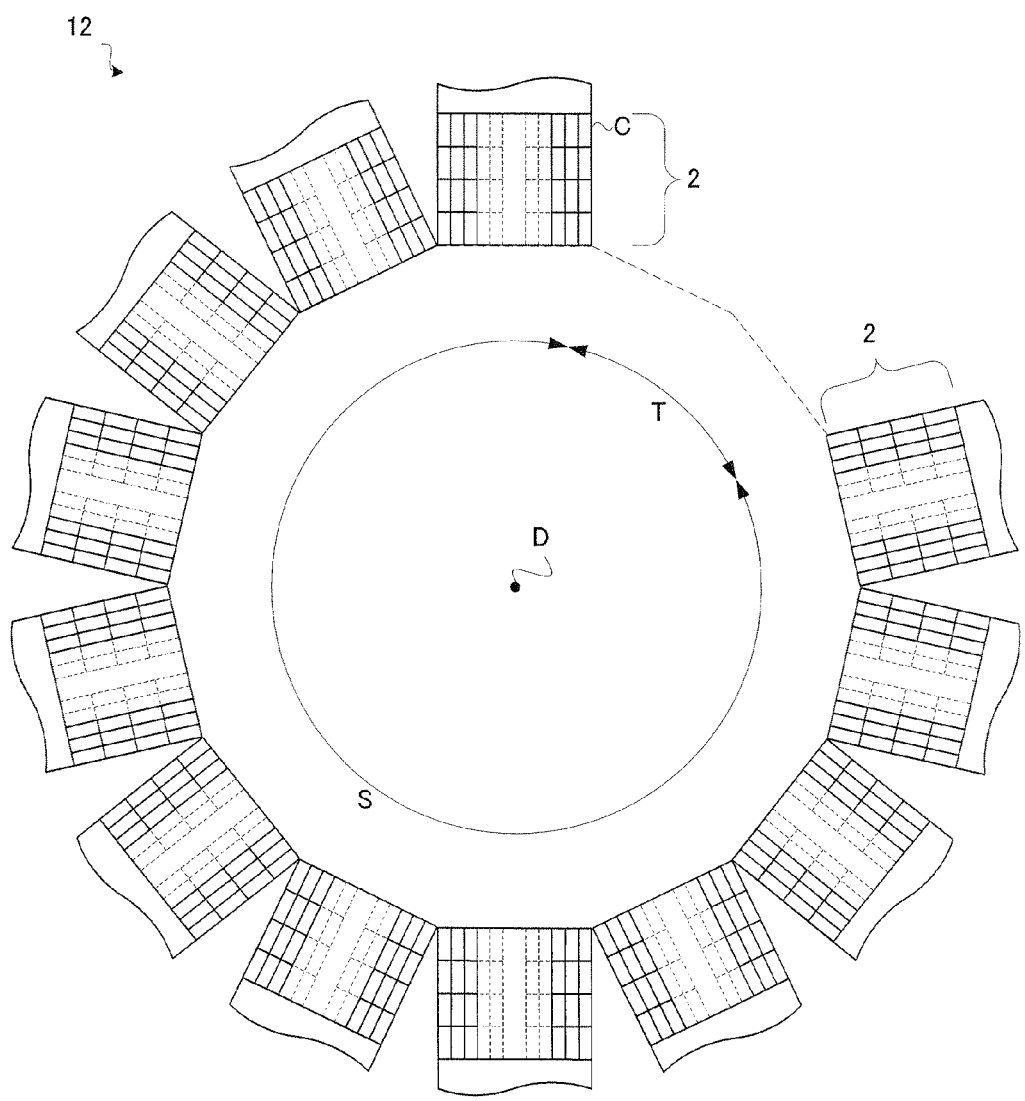
FIG. 4 is a plan view showing a configuration of a detector ring according to Embodiment 1.

FIG. 4 is a plan view showing a configuration of the detector ring according to Embodiment 1. Specifically, as shown in FIG. 4, the detector ring 12 has an array portion S having twelve radiation detectors 1 arranged in an arc shape following each side of the equilateral tetradecagon and a fracture portion T having no radiation detector 1, when seen in the axial direction. Let a center of curvature of the arc be a center of curvature D.

Figure 5:
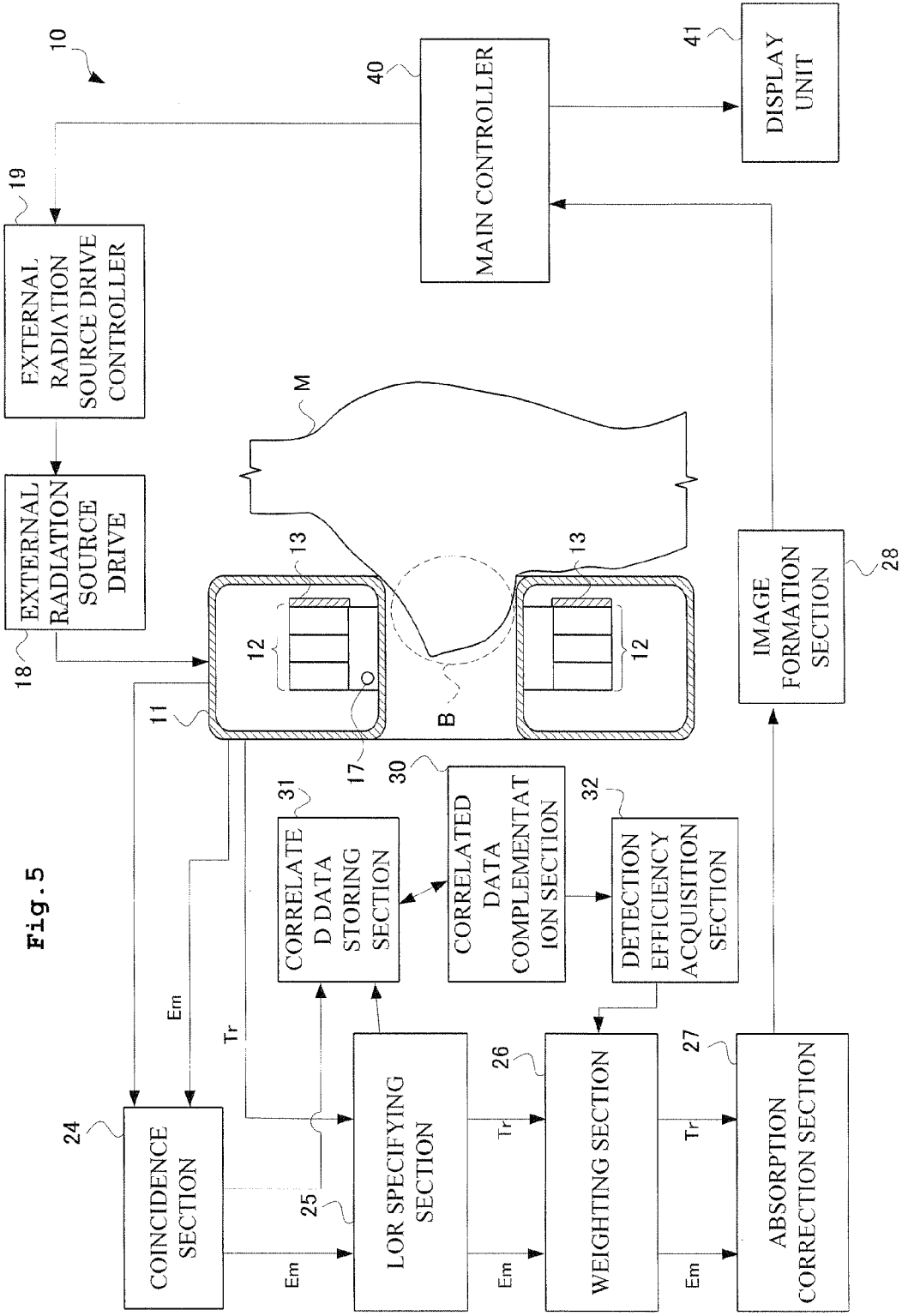
FIG. 5 is a functional block diagram showing a configuration of the radiation tomography apparatus according to Embodiment 1.

Description will be further given of a specific configuration of the radiation tomography apparatus 10. FIG. 5 is a functional block diagram showing a configuration of the radiation tomography apparatus according to Embodiment 1. As shown in FIG. 5, the radiation tomography apparatus 10 according to Embodiment 1 includes the gantry 11, the detector ring 12 in a C-shape provided inside of the gantry 11, a shield 13 in a C-shape for preventing radiation derived from outside of the gantry 11 from entering into the detector ring 12, an external radiation source 17 provided on an inner surface side of the detector ring 12 for applying fan beams of gamma rays, and an external radiation source drive 18 for driving thereof. Here, the external radiation source drive 18 is controlled under an external radiation source drive controller 19. The radiation tomography apparatus 10 further includes each section for obtaining sectional images of the site of interest B of the subject M. Specifically, the radiation tomography apparatus 10 includes a coincidence section 24 for receiving gamma ray detection signals showing a detection position, detection strength, and detection time of gamma rays from the detector ring 12 for performing coincidence of an annihilation gamma ray-pair, an LOR specifying section 25 for specifying an LOR based on two pieces of gamma ray detection data determined to be an annihilation-gamma-rays pair in the coincidence section 24, a weighting section 26 for weighting radiation detection intensity of acquired emission data and transmission data, an absorption correction section 27 for performing absorption correction of gamma rays with reference to transmission data mentioned later, and an image formation section 28 for forming a radiological image of the site of interest B. Here, the LOR specifying section corresponds to the position specifying device in this invention.

Description will be given of each configuration of the radiation tomography apparatus 10 that is needed for acquiring a map on a detection efficiency. As shown in FIG. 5, the radiation tomography apparatus 10 according to Embodiment 1 includes a correlated data storing section 31 for storing correlated information mentioned later, a correlated data complementation section 30 for complementing a number of coincident events in a fracture portion T by determining a number of coincident events under assumption that a scintillation counter crystal is in the fracture portion T, and a detection efficiency acquisition section 32 for acquiring a radiation detection efficiency in each radiation detecting element arranged in a detector ring by use of the number of coincident events and the number of coincident events through complementation. Here, the correlated data complementation section, the correlated data storing section, and the detection efficiency acquisition section correspond to the correlated data complementation device, the correlated data storing device, and the detection efficiency acquisition device, respectively.

The radiation tomography apparatus 10 according to Embodiment 1 further includes a main controller 40 for controlling such as the external radiation source drive controller 19 en bloc, and a display unit 41 for displaying a radiological image. The main controller 40 is formed of a CPU, and performs execution of various programs to realize the external radiation source drive controller 19, the coincidence section 24, the LOR specifying section 25, the absorption correction section 27, the image formation section 28, the correlated data complementation section 30, and the detection efficiency acquisition section 32.

The radiation tomography apparatus 10 may detect lack of uniformity of radiation detection efficiencies in each scintillation counter crystal based on the fan-sum method. Specifically, a map on detection efficiency is formed having mapped distribution of detection efficiencies of radiation in the entire detector ring 12. The weighting section 26 performs weighting of radiation detection intensity of emission data and transmission data in accordance with the map on detection efficiency.

Description will be given of a detection efficiency. Radiation detection performance may be lower than an ideal in fact even when radiation enters into the scintillation counter crystals C under the same condition. Consequently, the scintillation counter crystals C have variation in radiation detection performance. The reason for the above is, for example, due to a shape of the scintillation counter crystals C having a fractured corner thereof or a transparent material t having contamination thereon. The radiation detection performance varies in position of the scintillation counter crystals C in the scintillator 2. The radiation detection performance decreases toward a periphery of the scintillator 2. Here, use is made of a detection efficiency as an index for representing radiation detection performance of the scintillation counter crystals C. The detection efficiency is used for correcting and averaging differences in radiation detection performance of the scintillation counter crystals C.

Next, description will be given hereinafter of such configuration of the radiation tomography apparatus 10. Firstly, the radiation tomography apparatus 10 according to Embodiment 1 needs a map on detecting efficiency for obtaining a radiological image of the subject. Accordingly, description will be firstly given of each step to acquire the map on detecting efficiency.

Figure 6:
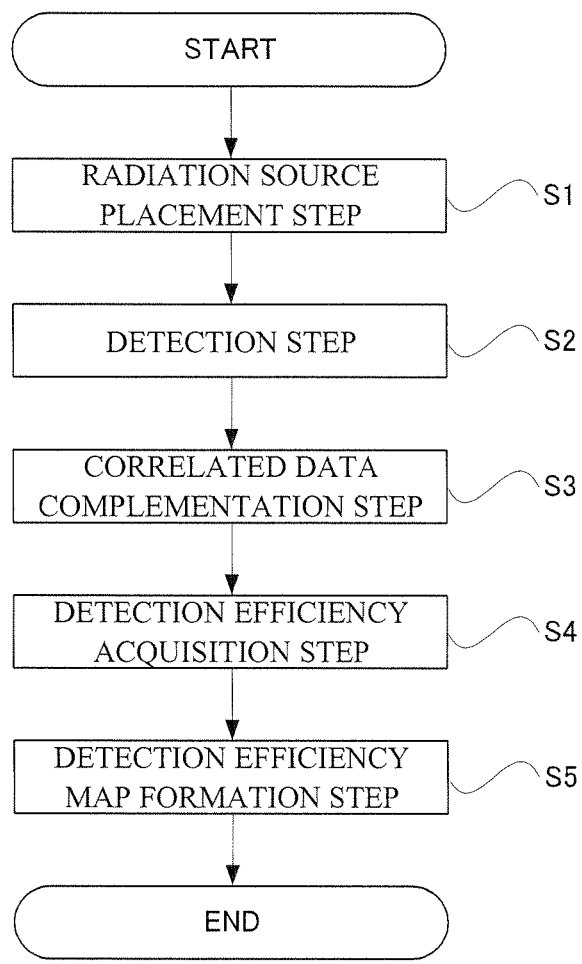
FIG. 6 is a flow chart showing a method of acquiring a map on a detection efficiency according to Embodiment 1.

As shown in FIG. 6, a method of acquiring a detection efficiency map according to Embodiment 1 includes a radiation source placement step S1 for placing a phantom inside a gantry 11, a detection step S2 for detecting an annihilation radiation-pair emitted from the phantom with a detector ring 12, a correlated data complementation step S3 for complementing a number of coincident events in a fracture portion T in accordance with the number of coincident events acquired in the previous step and an LOR corresponding thereto by determining a number of coincident events under assumption that a scintillation counter crystal C is in the fracture portion T, a detection efficiency acquisition step S4 for acquiring a radiation detection efficiency of each scintillation counter crystal C arranged in the detector ring 12 by use of the number of coincident events and the number of coincident events formed through complementation, and a detection efficiency map formation step S5 for forming a detection efficiency map through mapping of each detection efficiency according to an arrangement of each scintillation counter crystal C in the detector ring 12. Each of these steps will be described in order.

<Radiation Source Placement Step S1>

Firstly, the phantom is inserted into the opening of the gantry 11. The phantom contains positron emitting nuclides. Accordingly, a pair of annihilation radiation that travels in opposite directions to each other is emitted from the phantom toward the gantry 11. Here, the external radiation source 17 obstructive to acquisition of detection efficiencies is housed within a shielding unit not shown.

<Detection Step S2>

Firstly, description will be given of an LOR (line of response) prior to explanation on the detection step S2. The detector ring 12 has first and second scintillation counter crystals C. One of the pair of annihilation radiation emitting from the phantom strikes the first scintillation counter crystal C and the other strikes the second scintillation counter crystal C for conversion into fluorescence. That is, it may be determined from which point on a line connecting the first and second scintillation counter crystals C the annihilation radiation-pair has been emitted. The line connecting these scintillation counter crystals is called an LOR. In addition, the LOR corresponds to the positional information of this invention. The LOR is specified with the LOR specifying section 25.

Gamma-ray detection data is sent to the coincidence section 24. Where the first and second scintillation counter crystals Ca and Cb detect radiation within a time window having a given time width in the coincidence section 24, it is assumed that both scintillation counter crystals Ca and Cb coincidentally detect radiation. Moreover, the pair of radiation is considered an annihilation radiation-pair that travels in opposite directions to each other. Coincident detection of radiation as noted above with the first and second scintillation counter crystals Ca and Cb is called coincident event. The coincidence section 24 counts one as the annihilation radiation-pair is once counted in the first and second scintillation counter crystals Ca and Cb, and sends the count number to the correlated data storing section 31. As above, the correlated data storing section 31 stores a number of coincident events as a frequency where a pair of the first and second scintillation counter crystals Ca and Cb performs a coincident event. Simultaneously, the LOR specifying section 25 sends an LOR corresponding to the sent number of coincident events to the correlated data storing section 31. That is, the correlated data storing section 31 stores the number of coincident events in association with the LOR in the pair of the first and second scintillation counter crystals Ca and Cb. The correlated data storing section 31 stores the number of coincident events and the LOR corresponding thereto not only in the pair of the first and second scintillation counter crystals Ca and Cb but also in all possible pairs of scintillation counter crystals. Here, information formed in association with the number of coincident events and the LOR corresponding thereto is called correlated data.

In the detecting step S2, an annihilation radiation-pair is measured that is emitted from the phantom. Points where annihilation radiation pairs are generated are distributed throughout a cross section of the phantom. Consequently, painting of the LOR acquired in the detection step S2 on a sectional view of the phantom results in the view having a whole region painted with the LORs. The detector ring 12, however, has the fracture portion T. Accordingly, a close region to the fracture T in the phantom (hereinafter, referred to as a close region in phantom) has a thinner density of LOR painted.

<Correlated Data Complementation Step S3>

Next, the LOR through the close region of the phantom is complemented for compensating a deviation of the density of LOR due to existent fracture portion T. Specifically, when assuming that the scintillation counter crystal C is arranged in the fracture portion T, the number of coincident events on the scintillation counter crystal C arranged in the fracture portion T and correlated data formed of the LOR corresponding thereto is estimated using correlated data stored in the correlated data storing section 31.

In the correlated data complementation step S3, estimation is performed to the scintillation counter crystals C in the same position in the axial direction of the detector ring 12. That is, the number of coincident events is complemented using arrangement of the scintillation counter crystals C in a row in an arc shape. The scintillation counter crystals C in a row are called a unit detector ring 12a for expediency of explanation. The detector ring 12 has two radiation detectors 1p and 1q arranged in the axial direction of the detector ring 12. Thirty-two scintillation counter crystals C per single radiation detector 1 are arranged in the axial direction of the detector ring 12. Accordingly, the detector ring 12 may be divided into sixty-four unit detector rings 12a arranged to the axial direction thereof. In other words, the scintillation counter crystals C constitute the unit detector ring 12a having scintillation counter crystals C arranged at least in an arc shape in a row. Two or more detector rings 12a are stacked in the axial direction to form the detector ring 12.

The scintillator 2 provided in the radiation detector 1 has four scintillation counter crystal layers 2A to 2D. Description will be made hereinafter with the scintillator 2 having only one scintillation counter crystal layer for simple explanation.

Description will be given of operations in detail in the correlated data complementation step S3 according to Embodiment 1. Prior to this, twelve radiation detectors 1 in the detector ring 12 are numbered consecutively. Let a radiation detector 1 located in one end of the array of the radiation detectors 1 be the 0th one. Then the radiation detectors 1 are sequentially numbered. Let a radiation detector 1 located in the other end of the array be the 11th one.

Figure 7:
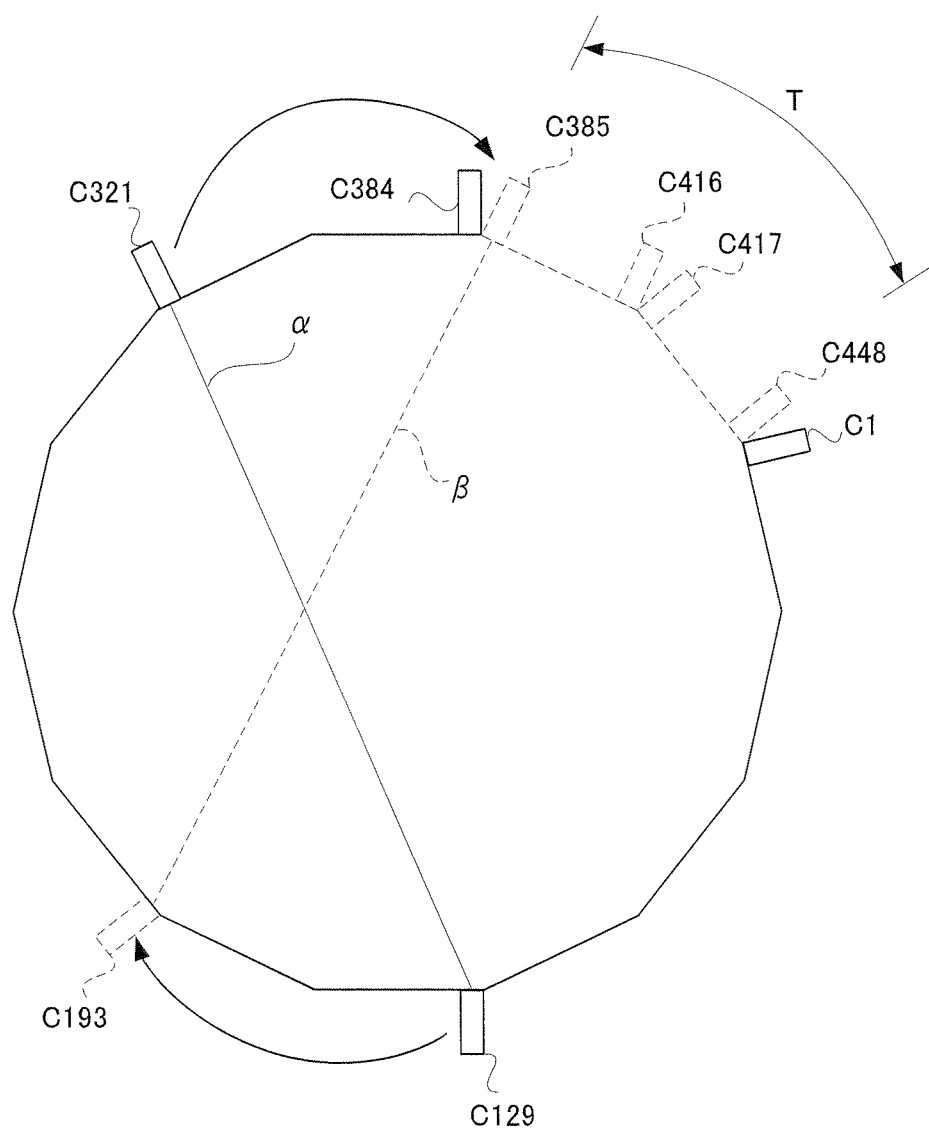
FIG. 7 is a schematic view showing a configuration of a unit detector ring according to Embodiment 1.
Figure 9:
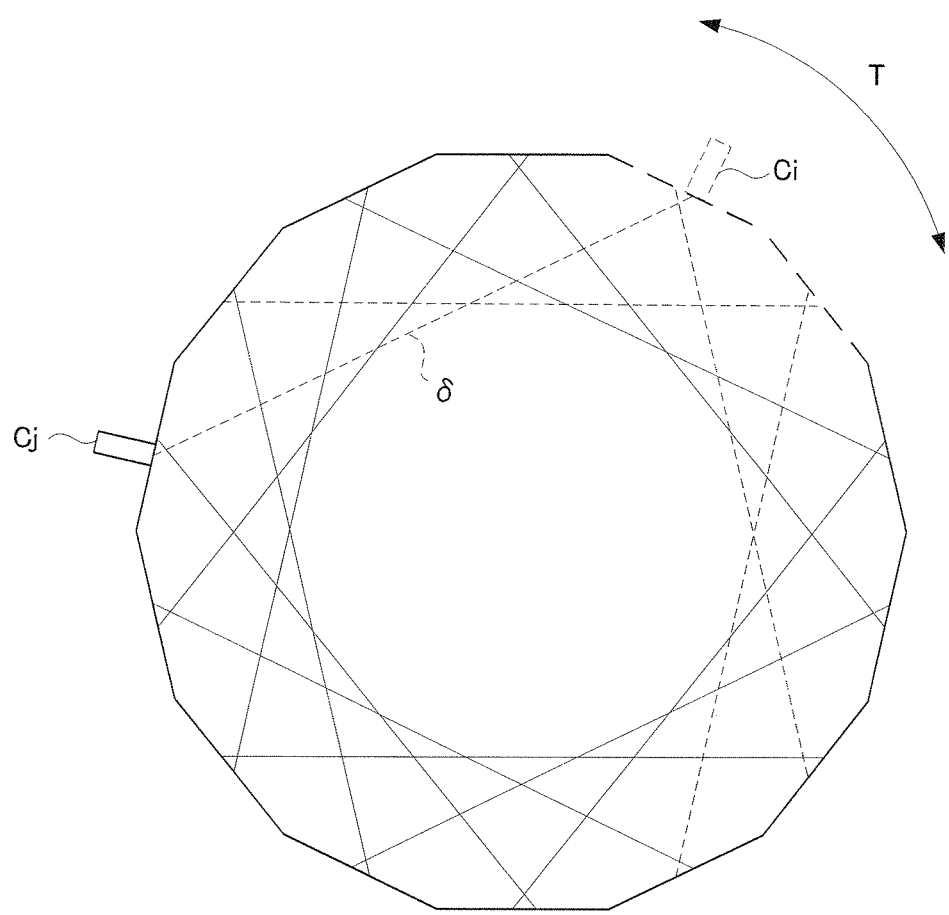
FIG. 9 is a schematic view showing a correlated data complement step according to Embodiment 1.

The scintillation counter crystals C arranged in the unit detector ring 12a are also numbered consecutively. FIG. 7 is a schematic view showing a configuration of the unit detector ring according to Embodiment 1. Specifically, let the scintillation counter crystal C be the first one that faces the fracture portion T among scintillation counter crystals C arranged in the 0th radiation detector 1. Subsequently, the scintillation counter crystals C are numbered across each radiation detector 1. Let the scintillation counter crystal C be the 384th one that faces the fracture portion T among scintillation counter crystals C arranged in the 11th radiation detector 1. That is, the scintillation counter crystal C having a number of multiples of thirty-two is to be located at the end of the scintillator 2 of the radiation detector 1.

Description will be given of a state where the number of coincident events is complemented. The unit detector ring 12a has only 384 scintillation counter crystals C. Here, it is assumed that the fracture portion T has the scintillation counter crystals C arranged at an equal pitch to that of the array portion S. Specifically, it is assumed that the 385th scintillation counter crystal C385 is arranged next to the 384th scintillation counter crystal. Subsequently, it is assumed that sixty-three scintillation counter crystals C386 to C448 are arranged between the scintillation counter crystals C1 and C385. Moreover, it is assumed that the scintillation counter crystals C385 to 416 are arranged in a row to form one side of the detector ring 12 having an equilateral tetradecagon. It is also assumed that the other scintillation counter crystals 417 to 448 are arranged in a row to form one side of the detector ring 12 having the equilateral tetradecagon. That is, the scintillation counter crystals 1 to 448 are arranged following each side of the equilateral tetradecagon. The arrangement of the scintillation counter crystals C is of fourteen-fold rotational symmetry about a center of curvature D.

Here, a number of coincident events is to be obtained that corresponds to an LOR β with the scintillation counter crystals C193 and C385. Since the scintillation counter crystal C385 does not actually exist, a number of coincident events corresponding to the LOR β is not measurable. The scintillation counter crystals 1 to 448 are arranged following each side of the equilateral tetradecagon, which results in LORs of rotational symmetry of the LOR β, for example an LOR α in FIG. 7. The LOR α is a line connecting the actual scintillation counter crystals C129 and C321. Herein, the scintillation counter crystal C193 in the LOR β corresponds to the scintillation counter crystal 129 in the LOR α. The scintillation counter crystal C385 in the LOR β corresponds to the scintillation counter crystal C321 in the LOR α. The LORs of rotational symmetry are considered to have the same number of coincident events.

The correlated data storing section 31 stores the number of coincident events and the corresponding LORs of all possible pairs of actual scintillation counter crystals C. Consequently, there certainly exists the number of coincident events corresponding to the LOR α.

In the configuration of Embodiment 1; the correlated data complementation section 30 reads out the number of coincident events corresponding to the LOR α from the correlated data storing section 31, and then correlates it with the LOR β to form correlated data. The data is added to the correlated data storing section 31. Specifically, according to the configuration of Embodiment 1, the correlated data is duplicated that corresponds to the LOR α, and is rewritten to be one that is counted in a pair of scintillation counter crystals C193 and C385, thereby allowing estimation of the number of coincident events and the positional information corresponding thereto under assumption that the scintillation counter crystal C321 is in the fracture portion T. In the correlated data complementation section 30, let the number of coincident events on the LOR β of the non-existent scintillation counter crystal C385 be a number of coincident events on the LOR α, thereby complementing data on the LOR in the close region of the phantom and the number of coincident events corresponding thereto. In other words, the correlated data complementation section 30 forms the number of coincident events and the LOR β corresponding thereto in accordance with the number of coincident events actually measured and stored in the correlated data storing section 31 and the LOR corresponding thereto under assumption that the scintillation counter crystal 321 is in the fracture portion T. The correlated data complementation section 30 complements the correlated data on the fracture portion T by additionally storing the formed number of coincident events and the LOR β corresponding thereto to the correlated data storing section 31.

Moreover, the following representation may be performed. That is, the correlated data complementation section 30 virtually rotates C129 and C321 while the relative position therebetween is maintained to make assumption that C321 is in the fracture portion T of the detector ring 12. Accordingly, the number of coincident events on the LOR β may be derived.

The correlated data complementation section 30 performs the same process to an LOR other than the above LOR α in which the number of coincident events is difficult to be measured actually. The following Equation 1 may be adopted for such process. Here, an LOR γ is to rotate that connects a non-existent scintillation counter crystal Ci and a scintillation counter crystal Cj.

$$m(i,j)=m(i+N_c x, j+N_c x) \quad (1)$$

Here, i and j is a numeral number of the scintillation counter crystal C including the virtual scintillation counter crystal C. Here in Embodiment 1, the number is an integer from 1 to 448. Here, m (i, j) expresses a number of coincident event in the scintillation counter crystals Ci and Cj. $N_c$ expresses how many scintillation counter crystals C per radiation detector 1 are arranged in the unit detector ring 12a. In Embodiment 1, thirty-two scintillation counter crystals are arranged on one side of the equilateral tetradecagon, and thus $N_c$=32. Here, x is an integer and expresses a rotation intensity of the LOR γ. Specifically, the LOR γ rotates x/14 times through a rotation movement illustrated in the above Equation 1. Accordingly, each of the scintillation counter crystals C having the LOR γ moves by x by 32 pieces of scintillation counter crystals as one scintillation counter crystal. In the embodiment of FIG. 7, x=2. That is, the scintillation counter crystal Ci virtually rotates over $N_c$ pieces of the scintillation counter crystals C, and conforms the scintillation counter crystal C having the LOR α of rotational symmetry of the LOR β.

In addition, $i+N_c x$ and $j+N_c x$ in Equation 1 is of an integer from 1 to 448. In Equation 1, simple calculation of $i+N_c x$ may give a value over 448. Here, the scintillation counter crystal C has a numeral number expressed by $i+N_c x$ that is a remainder left when $i+N_c x$ is divided by 448. For instance, let $i+N_c x$ be 449. As is seen from FIG. 7, this expresses the scintillation counter crystal C next to the scintillation counter crystal C448, and actually the scintillation counter crystal C1. Moreover, $j+N_c x$ is similar to the above.

In Embodiment 1, x is selected, and thereafter complementation is performed to the LOR and the number of coincident events corresponding thereto. The detector ring 12 has virtual 64 scintillation counter crystals C and existent 384 scintillation counter crystals C. Consequently, upon completion of the correlated data complementation step S3, the number of correlated data in association with the LOR and the number of coincident events stored in the correlated data storing section 31 increases through the complementation in comparison with that when the detection step S2 is completed.

<Detection Efficiency Acquisition Step S4>

The detection efficiency acquisition section 32 acquires a detection efficiency in each scintillation counter crystal by use of the correlated data in association with the LOR and the number of coincident events stored in the correlated data storing section 31. The fan-sum method as the conventional technique may be used for the above. FIG. 8 is a conceptual view showing operations of a detection efficiency acquisition section according to Embodiment 1. As shown in FIG. 8(a), for obtaining the detection efficiency in the scintillation counter crystal Cp, correlated data corresponding to two or more LORs 46 that extend in a fan shape from the scintillation counter crystal Cp as a center thereof is picked up from the correlated data storing section 31. Then, all the numbers of coincident events correlated with the picked up LORs 46 are added up. The total value thereof is divided by a number of the picked up LORs 46 to calculate a detection efficiency in the scintillation counter crystal Cp. The detection efficiency acquisition section 32 calculates detection efficiencies in such manner to every scintillation counter crystal Cp. That is, the same processing as above is, for example, to be repeated 383 times. However, the LORs having a shorter length are actually in no consideration for simple calculation. Accordingly, the actual repeat is to be performed less frequently.

Moreover, as shown in FIG. 8(b), for obtaining the detection efficiency in the scintillation counter crystal Cp, the correlated data storing section 31 picks up correlated data corresponding to two or more LORs 47 and 48 that extend in a fan shape from the scintillation counter crystal Cp as a center thereof. No number of coincident events in the LOR 48 corresponding thereto shown by dotted lines in FIG. 8(b) may actually be measured due to influence of the fracture portion T. According to the invention of Embodiment 1, however, the number of coincident events under assumption that the scintillator is in the fracture portion T has been acquired and complemented in the correlated data complementation step S3. Consequently, the detection efficiency acquisition section 32 may acquire the number of coincident events in the LOR 48 shown by dotted lines in FIG. 8(b) from the correlated data acquisition section 31. Here in FIG. 8, the number of the LORs that expands in a fan shape is omitted for simple explanation.

As is apparent from comparison of FIGS. 8(a) and 8(b), the fan region formed of two or more LORs may have an uniform shape in acquisition of the detection efficiencies in the scintillation counter crystals C. Consequently, calculation may be performed under the same condition that acquires the detection efficiencies in the scintillation counter crystals C belonging to a unit detector ring. That is because the fan region has a uniform shape independently of the scintillation counter crystals C through complementation of the number of coincident events that is not actually measurable.

As above, all detection efficiencies in every scintillation counter crystal C may be obtained that belongs to the unit detector ring 12a. Here, the detector ring 12 has sixty-four unit detector rings 12a. Accordingly, the foregoing operation is to be performed to each of the sixty-four unit detector rings.

<Detection Efficiency Map Formation Step S5>

Subsequently, a detection efficiency map is formed in arranging the detection efficiency of each scintillation counter crystal C acquired by detection efficiency acquisition step S4 in order of the scintillation counter crystal C. As noted above, a detection efficiency map according to Embodiment 1 may be acquired. The detection efficiency map is sent to the correlated data storing section 31 where it is stored.

Next, description will be given of an inspection method with the radiation tomography apparatus 10 according to Embodiment 1 with reference to FIG. 5. Upon conducting of inspections with the radiation tomography apparatus 10 according to Embodiment 1, firstly the site of interest B of the subject M (breast) is inserted into the opening of the gantry 11 with radiopharmaceutical being administered thereto by injection in advance. Next, transmission data showing absorption distributions of gamma rays within the site of interest B is obtained. Specifically, beams of gamma rays in a fan shape are applied from the external radiation source 17 towards the site of interest B. The gamma ray beams will pass through the site of interest B to be detected with the detector ring 12. Such detection is performed throughout the periphery of the site of interest B while rotating the external radiation source 17 along the inner surface of the detector ring 12 on the circular path, whereby an absorption map of gamma rays throughout the site of interest B is obtained.

Following obtaining of the transmission data as mentioned above, emission data is obtained to detect the annihilation gamma-rays pair that is emitted from the radiopharmaceutical located in the site of interest B. Prior to this, the external radiation source 17 obstructive of obtaining the emission data is moved in the axial direction of the detector ring 12 for storage thereof into a shielding unit not shown.

Thereafter, emission data is obtained. Specifically, the detector ring 12 detects an annihilation gamma-rays pair that is emitted from the inside of the site of interest B having traveling directions opposite. Gamma-ray detection signals detected with the detector ring 12 are sent to the coincidence unit 24. It is considered as one count only when two gamma ray photons are coincidentally detected in positions different to each other in the detector ring 12, and then subsequent data processing may be performed. Thereafter, such emission data is repeatedly obtained, which results acquisition of emission data with sufficient number of counts for imaging localization of the radiopharmaceutical inside the site of interest B. Finally, the site of interest B of the subject M is moved away from the opening of the gantry 11. An inspection is to be completed.

Next, description will be given of data processing in the radiation tomography apparatus according to Embodiment 1 with reference to FIG. 10. Transmission detection data Tr outputted from the detector ring 12 is sent out to the coincidence section 24. Here, the transmission detection data Tr and the emission detection data Em is sent to the LOR specifying section 25 for specifying an LOR. As noted above, the number of coincident events of gamma rays, transmission detection data Tr including information on the LOR, and emission detection data Em including the detection number of gamma rays and detection positions of gamma rays is formed and sent to the subsequent weighting section 26.

The weighting section 26 reads out a detection efficiency map from the correlated data storing section 31. Then, variations in detecting efficiency of the scintillation counter crystals C overlapping with the emission detection data Em and transmission detection data Tr are eliminated by use of the map. The transmission detection data Em and emission detection data Tr formed is sent to the absorption correction section 27.

The absorption correction section 27 performs absorption corrections to the emission detection data Em for eliminating influences of the gamma ray absorption distributions in the site of interest B that overlap with the emission detection data Em while referring to the transmission detection data Tr noted above. Thus, detection data showing radiopharmaceutical distributions in the site of interest B with more accuracy is sent to the image formation unit 28 where a radiological image is to be reconstructed. Finally, the display unit 41 displays the image. As noted above, an inspection with the radiation tomography apparatus 10 according to Embodiment 1 is to be completed.

As above, the detector ring 12 with the configuration of Embodiment 1 has the fracture portion T having no scintillation counter crystal C arranged therein. That is, the scintillation counter crystals C constituting the detector ring 12 are arranged with different rotational symmetry properties. When the fan-sum method is conventionally applied to such configuration, the detection efficiency is calculated under different conditions. That is because the scintillation counter crystals differ from one another in shape of the fan region for the fan-sum method. Accordingly, the calculated detection efficiency has no faithful reproducibility of the actual detection efficiency in the scintillation counter crystal C.

However, Embodiment 1 includes the correlated data complementation section 30. The correlated data complementation section 30 forms correlated data when assuming that the first scintillation counter crystal C actually provided in the detector ring 12 is in the fracture portion T, and additionally stores it to the correlated data storing section 31, thereby complementing correlated data in the fracture portion T. As noted above, the correlated data complementation section 30 obtains positional information under assumption that the scintillation counter crystals C are in the fracture portion T and the corresponding number of coincident events. Upon calculation of the detection efficiency with such configuration by use of the fan-sum method, the fan regions of the scintillation counter crystals C may be uniform for the fan-sum method. That is because complementation is made of the positional information that is not actually measurable due to the fracture portion T and the number of coincidence evens corresponding thereto (correlated data). Accordingly, the calculated detection efficiency of the scintillation counter crystal C according to Embodiment 1 has more faithful reproducibility of the actual detection efficiency. Weighting processing of the radiological image with such detection efficiency may ensure positive removal of lack of uniformity of radiation detection efficiencies in each of the scintillation counter crystals C overlapping with the radiological image. According to Embodiment 1, the radiation tomography apparatus may be provided that allows creation of radiological images suitable for diagnosis.

According to Embodiment 1, the complementation as noted above is performed by duplicating the correlated data stored with the correlated data storing section 31 and assuming that the duplication is counted in the fracture portion T. According to Embodiment 1, the correlated data is used that has already been stored in the data storing section. Consequently, the correlated data on the fracture portion T may positively be complemented. More particularly, in the configuration of Embodiment 1, the first and second scintillation counter crystals C belonging to the detector ring 12 rotate virtually while maintaining a relative position therebetween to assume that the first scintillation counter C is in the fracture portion T. That is, the correlated data complementation section 30 may readily complete complementation through assumption that the number of coincident events actually measured with the first and second scintillation counter crystals C belonging to the detector ring 12 is the number of coincident events in the fracture portion T.

Embodiment 2

Next, description will be given of a configuration of radiation tomography apparatus 10 according to Embodiment 2. Here, description will be omitted of a part of the radiation tomography apparatus 10 that is common to that in Embodiment 1. That is, Embodiment 2 has the same apparatus configuration as Embodiment 1.

Radiation tomography apparatus 10 according to Embodiment 2 differs from Embodiment 1 in complementation process of the number of coincident events. Accordingly, description will be given of a configuration unique to Embodiment 2 for performing a correlated data complementation step T3 instead of the correlated data complementation step S3 described in Embodiment 1.

<Correlated Data Complementation Step T3>

Moreover, in the configuration of Embodiment 2, the number of coincident events is complemented under assumption that the scintillation counter crystal C is in the fracture portion T through averaging of two or more numbers of coincident events, and assumption of the average to be counted in the fracture portion. That is, description will be given of a configuration for acquiring the number of coincident events in an LOR δ under assumption that the first scintillation counter crystal Ci is in the fracture portion T and the second scintillation counter Cj in the array portion where two sides of the equilateral tetradecagon adjacent to each other constitute the fracture portion T. It is assumed that the detector ring 12 has scintillation counter crystals C arranged in the fracture portion T. The scintillation counter crystals C are arranged following each side of the equilateral tetradecagon, which results in rotational symmetry of the LOR δ. Accordingly, there are thirteen LORs considered having the same number of coincident events as the LOR δ. However, the detector ring 12 actually has the fracture portion T. Thus, there are less LORs that allow counting. Specifically, let one of two adjacent sides of the equilateral tetradecagon that constitute the fracture portion T be a first side where it is assumed that the first scintillation counter crystal Ci exists, and the other be a second side. There are three types of LORs that are not countable due to no arranged scintillation counter crystal. That is, the LORs include an LOR obtained through rotation of the LOR δ to move the first scintillation counter crystal Ci into a position belonging to the second side through rotation of LOR δ, one to move the second scintillation counter crystal Cj into a position belonging to the first side, and one to move the second scintillation counter crystal Cj into a position belonging to the first side. That is, the number of coincident events is not coincidentally countable in three of thirteen LORs having rotational symmetry to the LOR δ.

Accordingly, the correlated data complementation section 30 in Embodiment 2 reads from the correlated data storing section 31 the number of coincident events corresponding to that in ten LORs where counting may be performed, and calculate an average thereof. In so doing, the average is considered the number of coincident events in the LOR δ under assumption that the first scintillation counter crystal Ci is in the fracture portion T and the second scintillation counter crystal Cj in the array portion S. The following Equation 2 may be adopted for such situation. Here, the number of coincident events in the LOR δ is to be obtained that connects a non-existent scintillation counter crystal Ci and a scintillation counter crystal Cj.

$$\langle m(i, j) \rangle = \frac{\sum_{x=0}^{N_b-1} m(i + N_c x, j + N_c x)}{N_b - 2A + N_a} \wedge \wedge \quad (2)$$

Here, i and j is a numeral number of the scintillation counter crystal C including the virtual scintillation counter crystal C. In Embodiment 2, the number is an integer from 1 to 448. Here, <m (i, j)> expresses a number of coincident event in the scintillation counter crystals Ci and Cj. $N_c$ expresses how many scintillation counter crystals C per radiation detector 1 are arranged in the unit detector ring 12a. In Embodiment 2, thirty-two scintillation counter crystals are arranged on one side of the equilateral tetradecagon, and thus $N_c$=32. Here, x is an integer and expresses a rotation intensity of the LOR δ. Specifically, the LOR δ rotates x/14 times to move into an LOR to be rotated. Accordingly, each of the scintillation counter crystals C in the LOR to which the LOR δ rotates moves by x by 32 pieces of scintillation counter crystals as one scintillation counter Crystal. Here, A expresses the number of fractures in the radiation detector 1. In Embodiment 2, two sides of the equilateral tetradecagon correspond to the fracture portion T, and thus A=2. Moreover, $N_b$ expresses the number of arrays in the radiation detector 1 including the fractured radiation detector 1. In Embodiment 2, the radiation detectors 1 are arranged following the equilateral tetradecagon, and thus $N_b$=14. Furthermore, $N_a$ expresses the number of LORs having both scintillation counter crystals Ci and Cj fractured in the LOR to which the LOR δ rotates in a range of 0<x<$N_b$. In the configuration of Embodiment 2, $N_a$=0.

Specifically, the correlated data complementation section 30 according to Embodiment 2 performs complementation of the number of coincident events in the fracture T as follows. That is, the scintillation counter crystals Ci and Cj virtually rotate while the relative position therebetween is maintained. The scintillation counter crystals C(i+$N_c$x) and C(j+$N_c$x) are collected as a pair of scintillation counter crystals C having rotational symmetry in positional relationship of the scintillation counter crystals Ci and Cj for obtaining and averaging the number of coincident events corresponding to ten sets of collected scintillation counter crystals C(i+$N_c$x) and C(j+$N_c$x). The average thereof is to be as the number of coincident events under assumption that the scintillation counter crystal Ci is in the fracture portion T. Here, the scintillation counter crystals C(i+$N_c$x) and C(j+$N_c$x) correspond to a pair of radiation detecting elements having rotational symmetry of this invention.

Complementation of the LOR that is not actually measurable with the configurations of Embodiments 1 and 2 may ensure accurate calculation of the detection efficiency in each scintillation counter crystal C. Such situation reproduced through simulations is to be described. FIGS. 10 to 13 are simulation results each showing effects on complementation according to Embodiments 1 and 2. In FIG. 10, a vertical axis indicates a detection efficiency, and a transverse axis indicates a numeral number of the scintillation counter crystal C belonging to a single unit detector ring 12a. FIG. 10(a) shows results when an detection efficiency of each scintillation counter crystal C is calculated while the radiation detectors 1 are arranged in the fracture portion T of the detector ring 12, and therefore fourteen radiation detectors are arranged annularly. FIG. 10(b) shows results when an detection efficiency of each scintillation counter crystal C is calculated without performing complementation of the number of coincident events while no radiation detector 1 is arranged in the fracture portion T of the detector ring 12. FIG. (10)c shows results when an detection efficiency of each scintillation counter crystal C is calculated through complementation of the number of coincident events based on the approach of Embodiment 1 while no radiation detector 1 is arranged in the fracture portion T of the detector ring 12. FIG. 10(d) shows results when an detection efficiency of each scintillation counter crystal C is calculated through complementation of the number of coincident events based on the approach of Embodiment 2 while no radiation detector 1 is arranged in the fracture portion T of the detector ring 12. Here, the results in FIG. 10 are all simulations on the first scintillation counter layer 2A of the scintillator 2.

FIGS. 10(a) and 10(b) differ from each other in profile thereof. That is because the fan regions used for the fan-sum method have a non-uniform shape throughout the scintillation counter crystals C although the detection efficiency is calculated with the fan-sum method. FIG. 10(c) shows the results when a detection efficiency is calculated based on the configuration of Embodiment 1 that performs complementation of the number of coincident events. Here, the profile of FIG. 10(c) is similar to that of FIG. 10(a) rather than that of FIG. 10(b). That is, in FIG. 10(c), the fan regions to be used in calculating the detection efficiency have a uniform shape throughout the scintillation counter crystals C. Consequently, the detection efficiency in the scintillation counter crystals C may be calculated more faithfully.

FIG. 10(d) shows the results when a detection efficiency is calculated based on the configuration of Embodiment 2 that performed complementation of the number of coincident events. Accordingly, the profile of graph form in FIG. 10(d) is similar to that in FIG. 10(a) rather than that in FIG. 10(b). That is, in FIG. 10(d), the fan regions to be used in calculating the detection efficiency have a uniform shape throughout the scintillation counter crystals C. Consequently, the detection efficiency in the scintillation counter crystals C may be calculated more faithfully.

FIG. 11 shows simulation results in the second scintillation counter layer 2B of the scintillator 2. Each requirement in FIGS. 11(a), 11(b), 11(c), and 11(d) is the same as that described in FIG. 10. FIG. 11 shows results through similar simulation as in FIG. 10 on the scintillation counter crystals C belonging to the second scintillation counter layer 2B of the radiation detector 1. Similar to FIG. 10, the detection efficiency in the scintillation counter crystals C may be calculated more faithfully in FIG. 11.

FIG. 12 shows simulation results in the third scintillation counter layer 2C of the scintillator 2. Each requirement in FIGS. 12(a), 12(b), 12(c), and 12(d) is the same as that described in FIG. 10. FIG. 12 shows results through similar simulation as in FIG. 10 on the scintillation counter crystals C belonging to the third scintillation counter layer 2C of the radiation detector 1. Similar to FIG. 10, the detection efficiency in the scintillation counter crystals C may be calculated more faithfully in FIG. 12.

FIG. 13 shows simulation results in the fourth scintillation counter layer 2D of the scintillator 2. Each requirement in FIGS. 13(a), 13(b), 13(c), and 13(d) is the same as that described in FIG. 10. FIG. 13 shows results through similar simulation as in FIG. 10 on the scintillation counter crystals C belonging to the fourth scintillation counter layer 2D of the radiation detector 1. Similar to FIG. 10, the detection efficiency in the scintillation counter crystals C may be calculated more faithfully in FIG. 13.

As noted above, according to the configuration of Embodiment 2, the correlated data complementation section 30 performs complementation through average of two or more numbers of coincident events and assumption of the averaging to be counted in the fracture portion T. In the configuration of Embodiment 2, the correlated data in the fractured portion T is complemented not in accordance with a single piece of correlated data but in accordance with two or more pieces of correlated data. Consequently, more positive complementation may be realized.

More particularly, the first and second scintillation counter crystals C rotate virtually while maintaining a relative position therebetween to collect a pair of scintillation counter crystals having rotational symmetry. The number of coincident events in the pair of scintillation counter crystals having rotational symmetry is considered equal to that in the pair of the first and second scintillation counter crystals C. That is because the pair of the scintillation counter crystals is same in its positional relationship. The number of coincident events suitable for complementation of correlated data in the fracture portion T may be surely determined through averages of the number of coincident events in such pair of scintillation counter crystals of rotational symmetry.

Embodiment 3

Next, description will be given of a configuration of radiation tomography apparatus 10 according to Embodiment 3. Here, description will be omitted of a part of the radiation tomography apparatus 10 according to Embodiment 3 that is common to that in Embodiment 1. That is, Embodiment 3 has the same apparatus configuration as Embodiment 1.

Radiation tomography apparatus 10 according to Embodiment 3 differs from Embodiment 1 in complementation process of the number of coincident events. Accordingly, description will be given of a configuration unique to Embodiment 3 for performing a correlated data complementation step U3 instead of the correlated data complementation step S3 described in Embodiment 1. Moreover, as shown in FIG. 14, the radiation tomography apparatus 10 according to Embodiment 3 has a number of coincident events correction section 33 provided therein for correcting the number of coincident events.

<Correlated Data Complementation Step U3>

The detector ring 12 has LORs of various lengths. In addition, the detector ring 12 has various angles with respect to the LORs. A position of the scintillation counter crystal C in the radiation detector 1 varies detection performance of fluorescence of the detector that is emitted through the scintillation counter crystal C. As above, the detection efficiency of the scintillation counter crystal C according to Embodiments 1 and 2 does not always correspond to a detection efficiency of radiation unique to the scintillation counter crystal C. That is, the detection efficiency in Embodiments 1 and 2 is influenced not only by an ability of the scintillation counter crystal C to convert radiation into fluorescence (hereinafter, referred to as a "conversion ability") but also by the length of the LOR as above. In Embodiment 3, the detection efficiency of each scintillation counter crystal C is acquired by use of the number of coincident events having the conversion ability with apparent variations corrected advance. In other words, the detection efficiency in Embodiment 3 corresponds to the conversion ability.

For instance, as shown in FIG. 10, the graph obtained through simulations described in Embodiment 1 has a profile with arches connected to one another at a pitch of the thirty-two scintillation counter crystals C. Such component in the arch shape occurs for the reason, independently of the conversion ability, that the side end of the scintillator 2 of the radiation detector 1 has low detecting sensitivity of radiation. Such apparent variations in conversion ability due to different LORs may be eliminated through correcting of the number of coincident events performed in Embodiments 1 and 2. The number of coincident events correcting section 33 temporarily reads from the correlated data storing section 31 the correlated data including the number of coincident events for performing a given correction to form corrected data. Thereafter, the correlated data storing section 31 stores the corrected data. The number of coincident events correcting section 33 has apparent patterns of variations in conversion ability that varies dependently of the LOR, and forms corrected data from the correlated data based on the patterns. The number of coincident events in the LORs that is not actually measurable may be complemented also in Embodiment 3. Specific method therefor is once correcting all numbers of coincident events in the detectable LORs and then acquiring an average thereof. Here, the average is referred to as an average of the number of coincident events. The detection efficiency of the scintillation counter crystal C (conversion ability) on the LORs that is not influenced by environments is obtained as the number of coincident events in the LORs in which the average of the number of coincident events is not actually measurable. The average is acquired by the correlated data complementation section 30. In Embodiment 3, calculation may be performed that acquires the detection efficiencies $\epsilon_{ui}$ in the scintillation counter crystal Ci belonging to a unit detector ring u by use of the following equation.

$$\varepsilon_{ui}^{k} = \frac{\sum_{v,j \in fan\_i} m'^{(k)}(u, i, v, j)}{\sum_{v,j \in fan\_i} \varepsilon_{vj}^{k-1}} \Lambda\Lambda \quad (3)$$

Here, fan_i expresses the fan region having a cone shape with a centered scintillation counter crystal Ci. Accordingly, the LORs belonging to the fan_i also includes the LORs of the scintillation counter crystal Ci and any scintillation counter crystal C that does not belong to the unit detector ring u. In the correlated data complementation step S3 according to Embodiment 1, only the scintillation counter crystals C belonging to the unit detector ring 12a are processed. On the other hand, the configuration according to Embodiment 3 differs from the above in that the number of coincident events is complemented also with reference to the LORs across the unit detector ring 12a.

In actual operation, it is temporarily assumed that a detection efficiency $\varepsilon^{0}_{vj}$ of the scintillation counter crystal Cvj belonging to the fan_i is of 1. Here, the scintillation counter crystal Cvj includes a virtual scintillation counter crystal C. The scintillation counter crystal Cvj corresponds to the scintillation counter crystal Cj belonging to the unit detector ring v.

Next, description will be given of the numerator in Equation 3. Here, $m'^{(k)}(u, i, v, j)$ expresses the number of coincident events corresponding to the LOR of the scintillation counter crystal Cui belonging to the unit detector ring u and the scintillation counter crystal Cvj belonging to unit detector ring v that are acquired through the k-th calculation. In addition, m' expresses the number of coincident events corrected by the number of coincident events correcting section 33. That is, the numerator in Equation 3 means that addition is made of the corrected number of coincident events corresponding to the LOR belonging to fan_i.

All the numbers of coincident events in the detectable LORs are temporarily corrected. Accordingly, apparent variations in conversion ability of the scintillation counter crystal C to convert radiation into fluorescence are corrected in advance. Consequently, all the LORs are under the same condition except for the unique conversion ability of the scintillation counter crystal C.

Here, j in Equation 3 is a population including existent scintillation counter crystal C and the virtual scintillation counter crystal C. Among them, components j as virtual scintillation counter crystals C are selected to be a new population $m'^{(k)}(u, i, v, j_0)$. Then, m' (k) (u, i, v, j_0) may be expressed with the following Equation 4.

$$m'^{(k)}(u,i,v,j_0) = m'_{ave}(u,i,v,j)\varepsilon_{ui}^{(k-1)}\varepsilon_{j_0}^{(0)}\Lambda\Lambda \quad (4)$$

Here, $m'^{(k)}(u, i, v, j_0)$ expresses the number of coincident events acquired through the k-th calculation. Here, $m'_{ave}(u, v, i, j)$ expresses the average of the number of coincident events counted in the existent scintillation counter crystals C. $\varepsilon^{(k-1)}_{ui}$ is a detection efficiency of the existent scintillation counter crystal Ci acquired by the previous calculation, i.e., the k–1 th calculation. $\varepsilon^{(0)}_{j_0}$ is a detection efficiency (fixed value) of the virtual scintillation counter crystal Cj_0. In addition, the existent scintillation counter crystal C forms j in $m'_{ave}(u, v, i, j)$.

In Embodiment 3, $\varepsilon_{ui}$ is acquired in advance in such manner, and then substituted for the denominator in Equation 3 for obtaining new $\varepsilon_{ui}$. Let the last calculated result be $\varepsilon^{(k-1)}$, this calculated result may be expressed as $\varepsilon^{k}$. The values of the detection efficiencies $\varepsilon^{0}_{vj}$ are all 1, and calculation of the detection efficiency $\varepsilon_{vj}$ is repeated by using Equation 3, which results in a more reliable value of $\varepsilon^{k}_{vj}$. Such calculation process of the detection efficiency $\varepsilon^{k}_{vj}$ is called an iterative fan-sum method. Here, the detection efficiency of the virtual scintillation counter crystal C included in the denominator in Equation 3 has a fixed value of 1 independently of the iterations to be performed.

Figure 15:
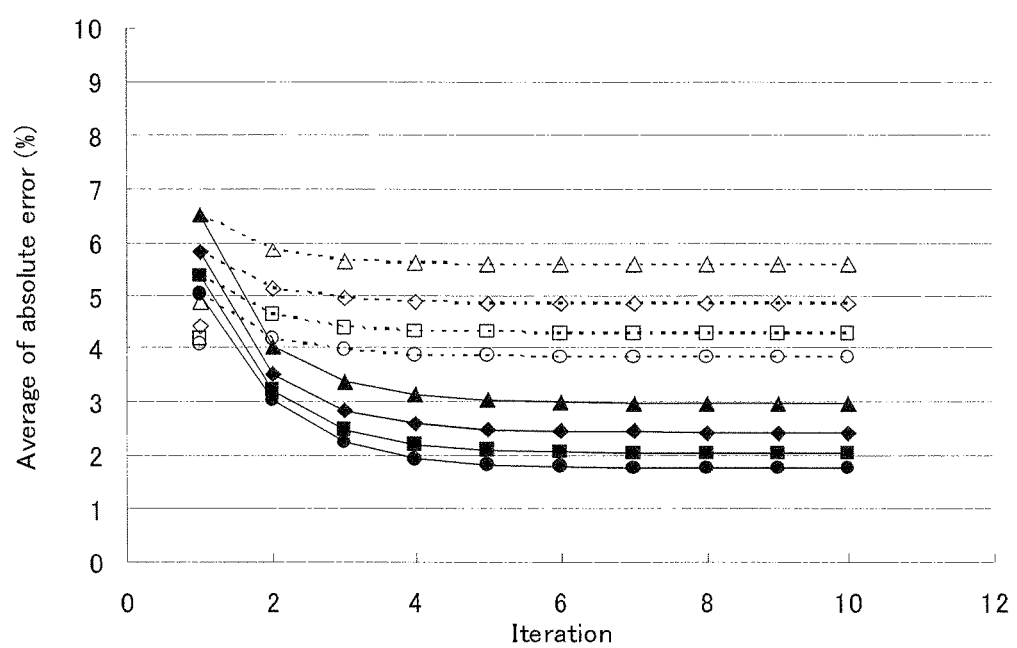
FIG. 15 is a simulation result showing effects on complementation according to Embodiment 3.

Effects of the complementation in Embodiment 3 through simulations is to be described. FIG. 15 is a simulation result showing effects on complementation according to Embodiment 3. Firstly, the detection efficiency of the scintillation counter crystals C of the detector ring 12 is determined in advance having given variations. Then, the number of coincident events in each LOR is acquired through simulations based on the above, and is corrected so as not to be influenced by the environment with respect to the LOR. Such correction corresponds to that in the number of coincident events correcting section 33. Thereafter, the corrected number of coincident events is substituted for the denominator in Equation 3 for obtaining new $\varepsilon^{k}_{vj}$.

In FIG. 15, a round mark expresses a calculated result in the first scintillation counter crystal layer 2A, and a square mark expresses a calculated result in the second scintillation counter crystal layer 2B. Moreover, a triangle mark expresses a calculated result in the third scintillation counter crystal layer 2C, and a cross mark expresses a calculated result in the fourth scintillation counter crystal layer 2D. Furthermore, a transverse axis expresses an iteration k. A vertical axis expresses errors between the detection efficiency of the scintillation counter crystal C calculated with the Equation 3 and the detection efficiency of the scintillation counter crystal C determined in advance. Smaller error indicates faithful reproduction of the detection efficiency determined in advance.

FIG. 15 shows comparison results on the detection efficiency $\varepsilon^{k}_{vj}$ in which an open mark expresses calculated detection efficiency by the conventional fan-sum method, an open mark with dotted lines expresses that by the iterative fan-sum method having a uniform number of coincident events to be complemented, and a solid mark with solid lines expresses that by the iterative fan-sum method for performing complementation with the renewed number of coincident events based on Equations 3 and 4. As is seen from the calculated results in the first scintillation counter crystal 2A in FIG. 15, errors in the detection efficiency $\varepsilon^{k}_{vj}$ obtained by the conventional fan-sum method fall around 4.0%, whereas errors in the detection efficiency $\varepsilon^{k}_{vj}$ obtained by the iterative fan-sum method to complement the renewed number of coincident events fall around 1.8% as the iteration k increases. As noted above, the detection efficiency $\varepsilon^{k}_{vj}$ obtained under the configuration of Embodiment 3 is more faithful to the detection efficiency of the actual scintillation counter crystal C.

That is, according to Embodiment 3, the correlated data complementation section 30 complements a number of coincident events in the fracture portion T by correcting the number of coincident events acquired from the scintillation counter crystal C constituting the unit detector ring 12a and averaging them for determining an average of the number of coincident events, and by assuming it to be counted in the fracture portion T. The detection efficiency acquisition section 32 once sets a detection efficiency of the radiation detecting elements arranged in the array portion S to be a predetermined value, and sets a detection efficiency of the scintillation counter crystal C assumed to be in the fracture portion T to be a value of 1 for calculating a detection efficiency of the scintillation counter crystal C arranged in the array portion S based on the corrected number of coincident events and the average of the number of coincident events. The detector efficiency acquisition section 32 acquires again a detection efficiency of the scintillation counter crystal C arranged in the array portion S based on the acquired detection efficiency of the scintillation counter crystal C and the detection efficiency of the scintillation counter crystal C assumed to be in the fracture portion T. Here, let the number of coincident events assumed to be counted in the fracture portion T be one that is obtained by multiplying the average of the number of coincident events calculated firstly by the detection efficiency of the scintillation counter crystal C calculated through previous calculation. The detection efficiency of the scintillation counter crystal C assumed to be in the fracture portion T is constant at a value of 1. Here, setting of the detection efficiency of the scintillation counter crystal C arranged in the array portion S and that of the scintillation counter crystal C assumed to be in the fracture portion T to be a value of 1 corresponds to setting of the predetermined value to be a value of 1 in this invention.

Figure 16:
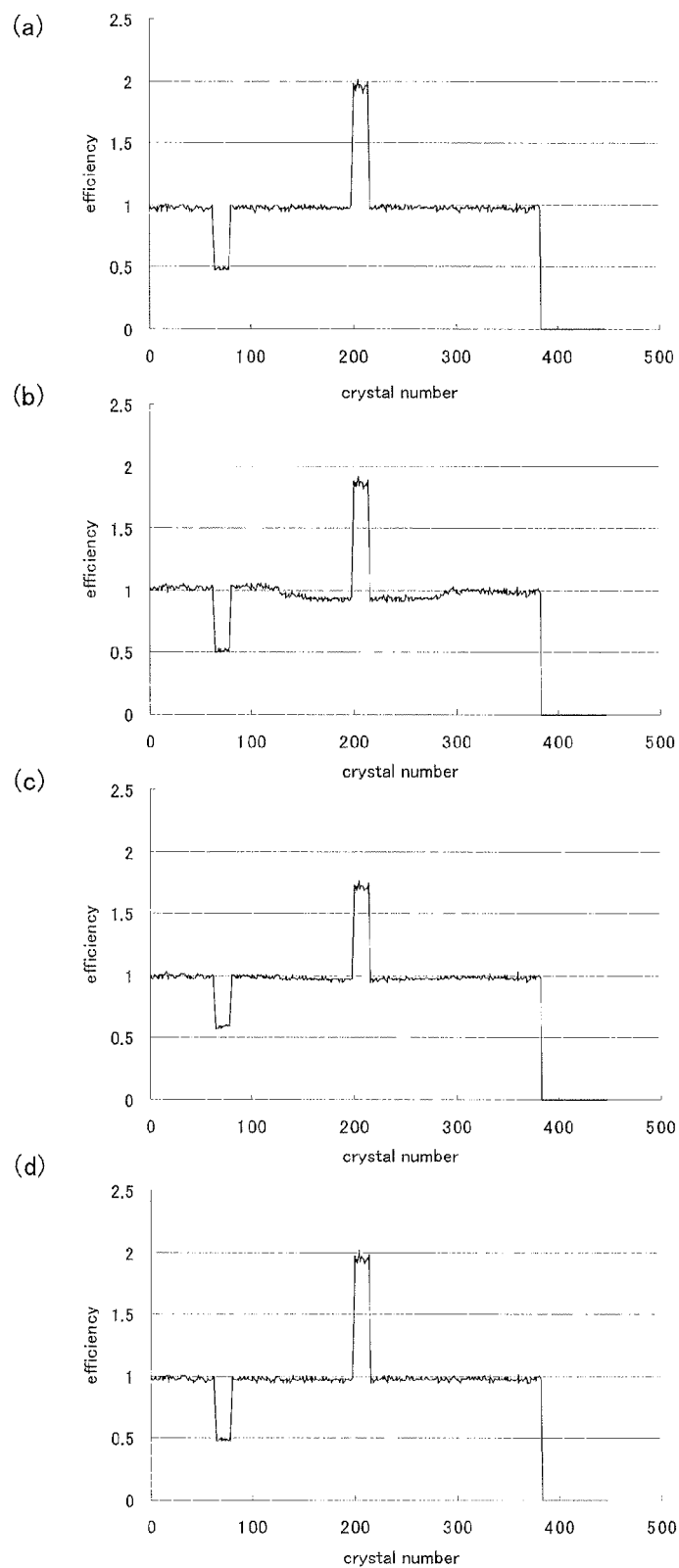
FIGS. 16 to 19 are simulation results of comparison between detection efficiencies according to Embodiment 3.

The effect in the configuration of Embodiment 3 is to be described from another point of view. FIG. 16 is a simulation result of comparison of detection efficiencies according to Embodiment 3. In FIG. 16, a vertical axis indicates a detection efficiency of the scintillation counter crystal C belonging to a unit detector ring 12a, and a transverse axis indicates a numeral number of the scintillation counter crystal C belonging to a single unit detector ring 12a. FIG. 16(c) and (d) is a simulation of the unit detector ring 12a located in the middle of the scintillation counter crystal layer 2A having the scintillation counter crystals C arranged two-dimensionally with the detection efficiency k of 10. FIG. 16(a) shows a unique detection efficiency (conversion ability) of the scintillation counter crystal C. FIG. 16(b) shows results from the conventional fan-sum method when an detection efficiency of each scintillation counter crystal C is calculated without performing complementation of the number of coincident events while no radiation detector 1 is arranged in the fracture portion T of the detector ring 12. FIG. 16(c) shows results when an detection efficiency of each scintillation counter crystal C is calculated through complementation of the number of coincident events having a fixed value based on the approach of Embodiment 3 while the radiation detector 1 is arranged in the fracture portion T of the detector ring 12. FIG. 16(d) shows results when a detection efficiency of each scintillation counter crystal C is calculated through complementation with the renewed number of coincident events based on the approach of Embodiment 3 while the radiation detector 1 is arranged in the fracture portion T of the detector ring 12. As is apparent through comparison of FIGS. 16(a) and 16(b), the detection efficiency acquired by the fan-sum method is disturbed due to the fracture portion T of the detector ring 12. As is seen from FIGS. 16(a) and 16(c), the detection efficiency is converged in a position derived from the original one so as not to renew the number of coincident events.

As is apparent through comparison of FIGS. 16(a) and 16(d), the configuration of Embodiment 3 acquires the detection efficiency close to the actual one by the iterative fan-sum method even when the detector ring 12 has the fracture portion T.

Figure 17:
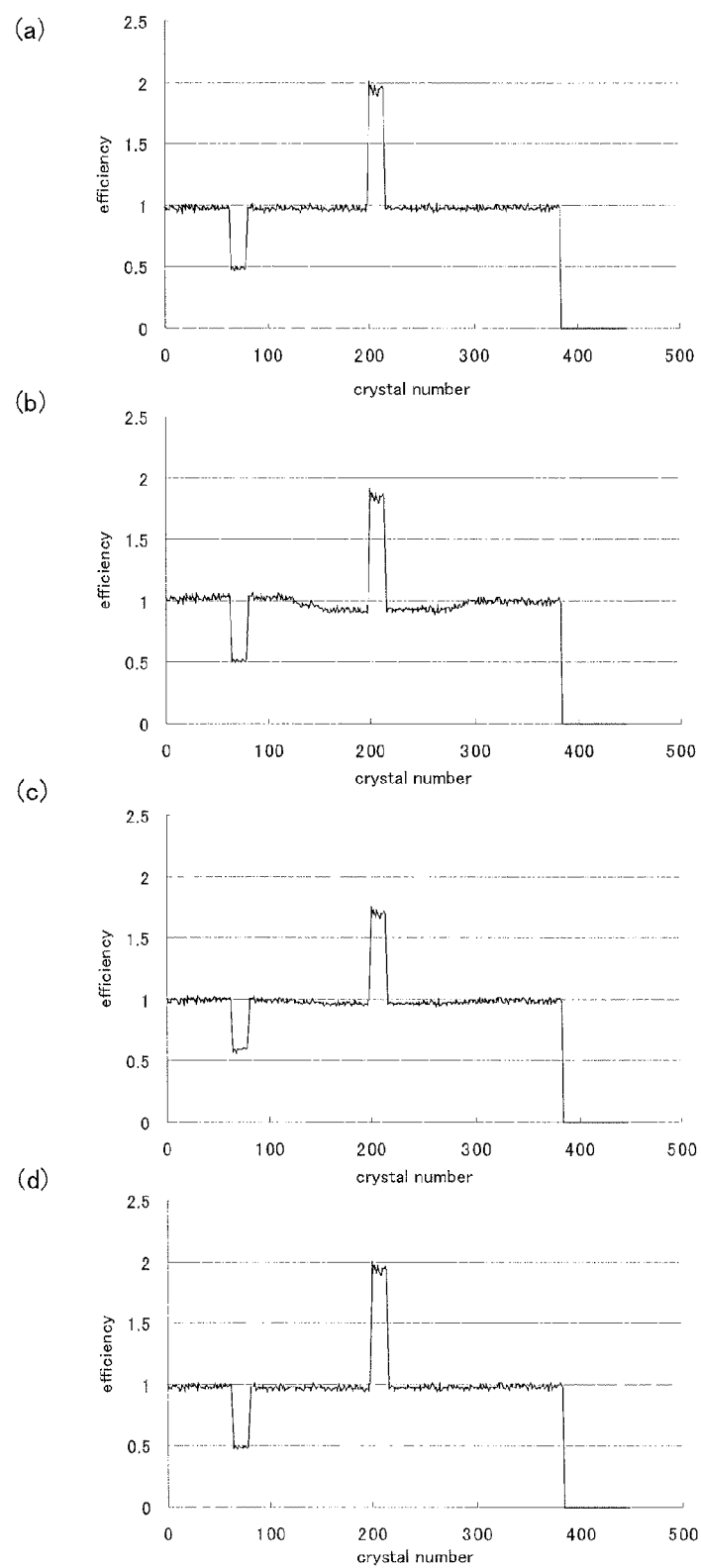

FIG. 17 shows simulation results in the second scintillation counter layer 2B of the scintillator 2. Each requirement in FIGS. 17(a), 17(b), 17(c), and 17(d) is the same as that described in FIG. 16. FIG. 17 shows results through similar simulation as in FIG. 16 on the scintillation counter crystals C belonging to the second scintillation counter layer 2B of the radiation detector 1. Similar to FIG. 16, the detection efficiency in the scintillation counter crystals C may be calculated more faithfully in FIG. 17.

Figure 18:
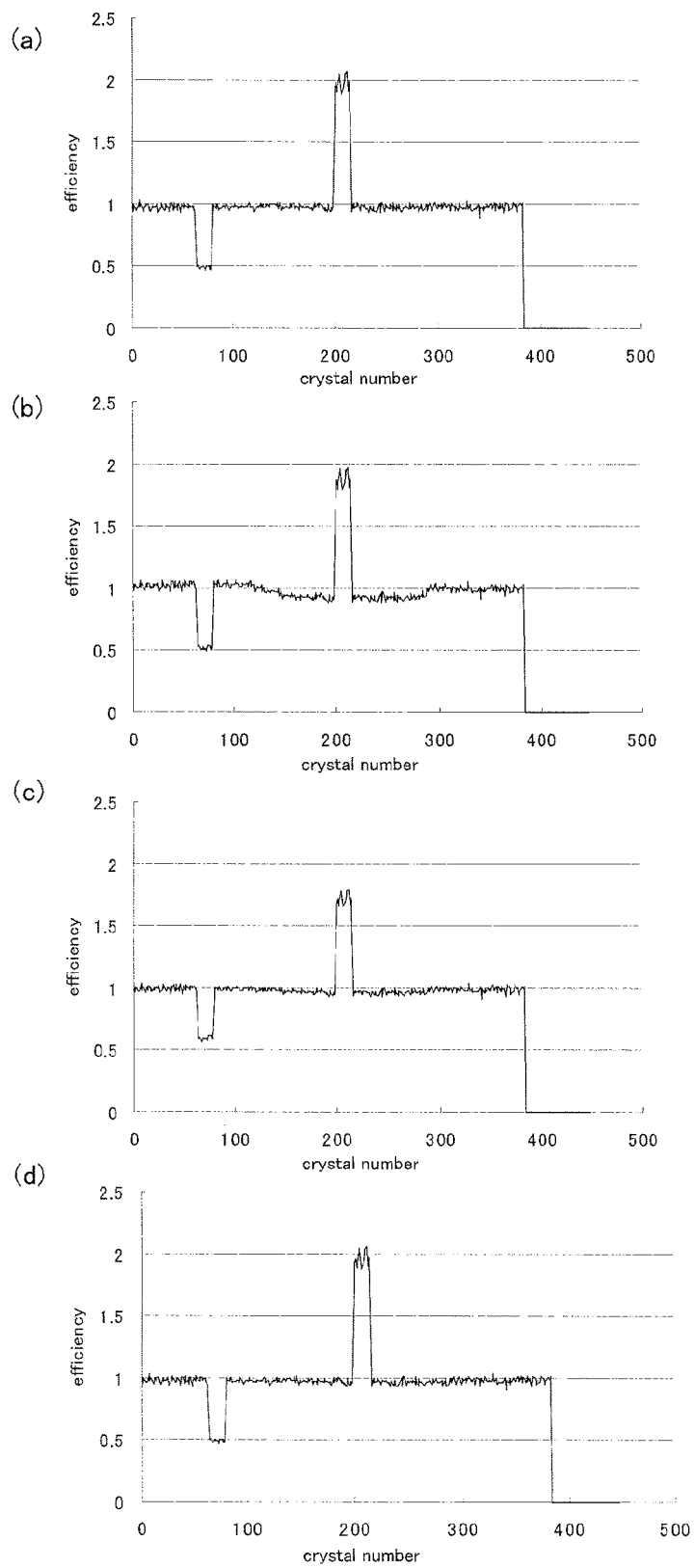

FIG. 18 shows simulation results in the third scintillation counter layer 2C of the scintillator 2. Each requirement in FIGS. 18(a), 183(b), 18(c), and 18(d) is the same as that described in FIG. 16. FIG. 18 shows results through similar simulation as in FIG. 16 on the scintillation counter crystals C belonging to the third scintillation counter layer 2C of the radiation detector 1. Similar to FIG. 16, the detection efficiency in the scintillation counter crystals C may be calculated more faithfully in FIG. 18.

Figure 19:
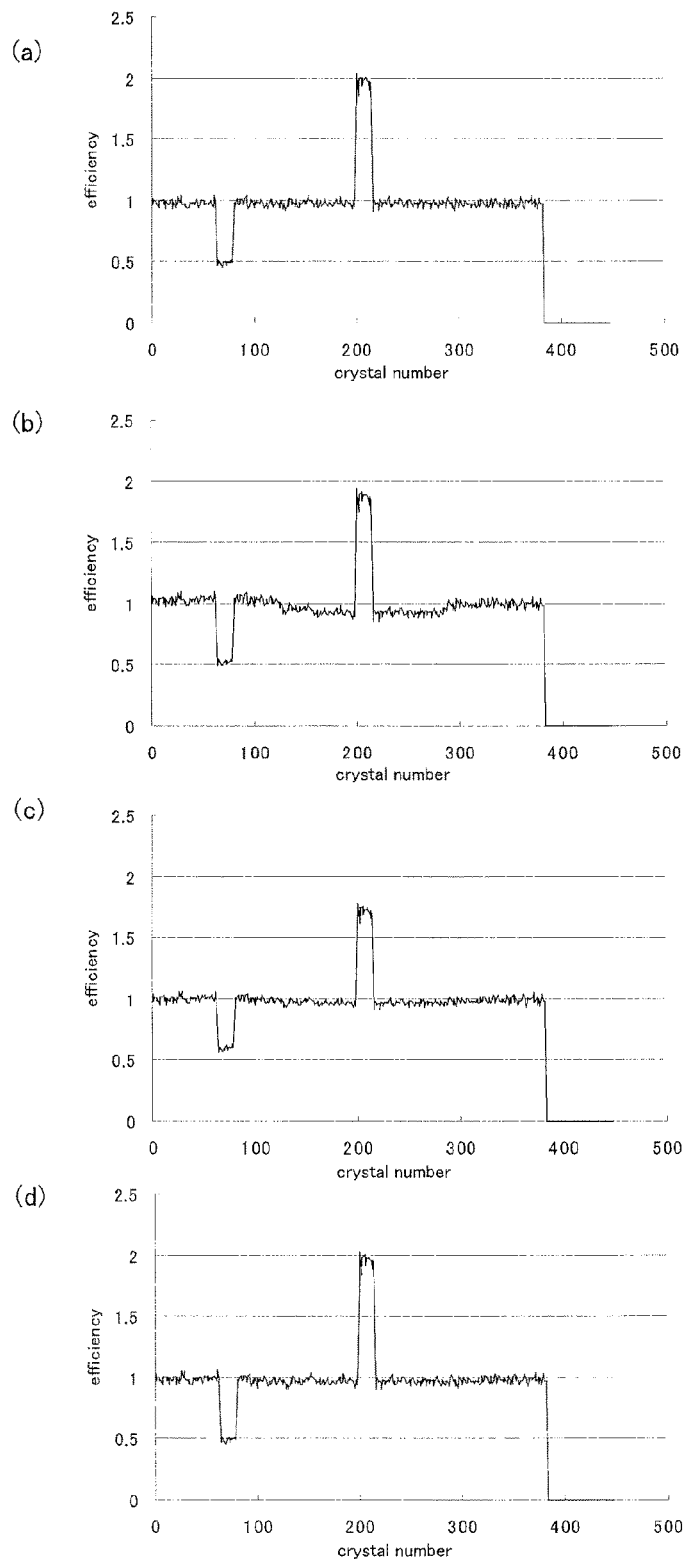

FIG. 19 shows simulation results in the fourth scintillation counter layer 2D of the scintillator 2. Each requirement in FIGS. 19(a), 19(b), 19(c), and 19(d) is the same as that described in FIG. 16. FIG. 19 shows results through similar simulation as in FIG. 16 on the scintillation counter crystals C belonging to the fourth scintillation counter layer 2D of the radiation detector 1. Similar to FIG. 16, the detection efficiency in the scintillation counter crystals C may be calculated more faithfully in FIG. 19.

According to the foregoing construction in Embodiment 3, a method of calculating the detection efficiency may be provided that is different from that calculations in Embodiments 1 and 2. According to Embodiment 3, the number of coincident events is temporarily complemented, which results in simple calculation for obtaining the detection efficiency. Moreover, the detection efficiency is calculated in consideration of the LORs across the unit detector ring 12a. Accordingly, Embodiment 3 may be more advantageous than Embodiments 1 and 2 in its calculation method.

This invention is not limited to the foregoing embodiments, but may be modified as follows:

(1) In the above Embodiment 1, the LOR γ has thirteen rotatable LORs. The number of coincident events in the LOR γ is acquired through duplication of the number of coincident events in the ten LORs among them in which the number of coincident events may actually be counted. However, this invention is not limited to such configuration. Where the scintillators are arranged in a circular shape along a virtual circle in the detector ring 12, the LOR of rotary symmetry to the LOR γ does not appear over thirty-two scintillation counter crystals C, but the scintillation counter crystal C(i+1) next to the scintillation counter crystal Ci has the LOR of rotary symmetry to the LOR γ. In such situation, the following Equation 5 may be adopted instead of the foregoing Equation 1.

$$m(i,j)=m(i+x,j+x) \tag{5}$$

(2) In the above Embodiment 2, the LOR δ has thirteen rotatable LORs. The number of coincident events in the LOR δ is acquired through averaging of the number of coincident events in the LORs among them in which the number of coincident events may actually be counted. However, this invention is not limited to such configuration. Where the scintillators are arranged in a circular shape along a virtual circle in the detector ring 12, the LOR of rotary symmetry to the LOR δ does not appear over thirty-two scintillation counter crystals C, but the scintillation counter crystal C(i+1) next to the scintillation counter crystal Ci has the LOR of rotary symmetry to the LOR δ. In such situation, the following Equation 6 may be adopted instead of the foregoing Equation 2. Here, $N_d$ expresses the number of the scintillation counter crystals C arranged in the unit detector ring 12a.

$$\langle m(i,j) \rangle = \frac{\sum_{x=0}^{N_d-1} m(i+x, j+x)}{N_d - 2A + N_a} \Lambda\Lambda \tag{6}$$

(3) in each of the foregoing embodiment, the scintillation counter crystal is composed of LYSO. Alternatively, the scintillation counter crystal may be composed of another materials, such as GSO ($Gd_2SiO_5$), may be used in this invention. According to this modification, a method of manufacturing a radiation detector may be provide that allows provision of a radiation detector of low price.

(4) In each of the foregoing embodiments, the scintillator 4 has four scintillation counter crystal layers. This invention is not limited to the embodiments. For instance, the scintillator formed of one scintillation counter crystal layer may be applied to this invention. Moreover, the scintillation counter crystal layer may be freely adjusted in number depending on applications of the radiation detector.

(5) The fluorescence detector in each of the foregoing embodiment is formed of the photomultiplier tube. This invention is not limited to the embodiments. A photodiode or an avalanche photodiode, etc. may be used instead of the photomultiplier tube.

Figure 20:
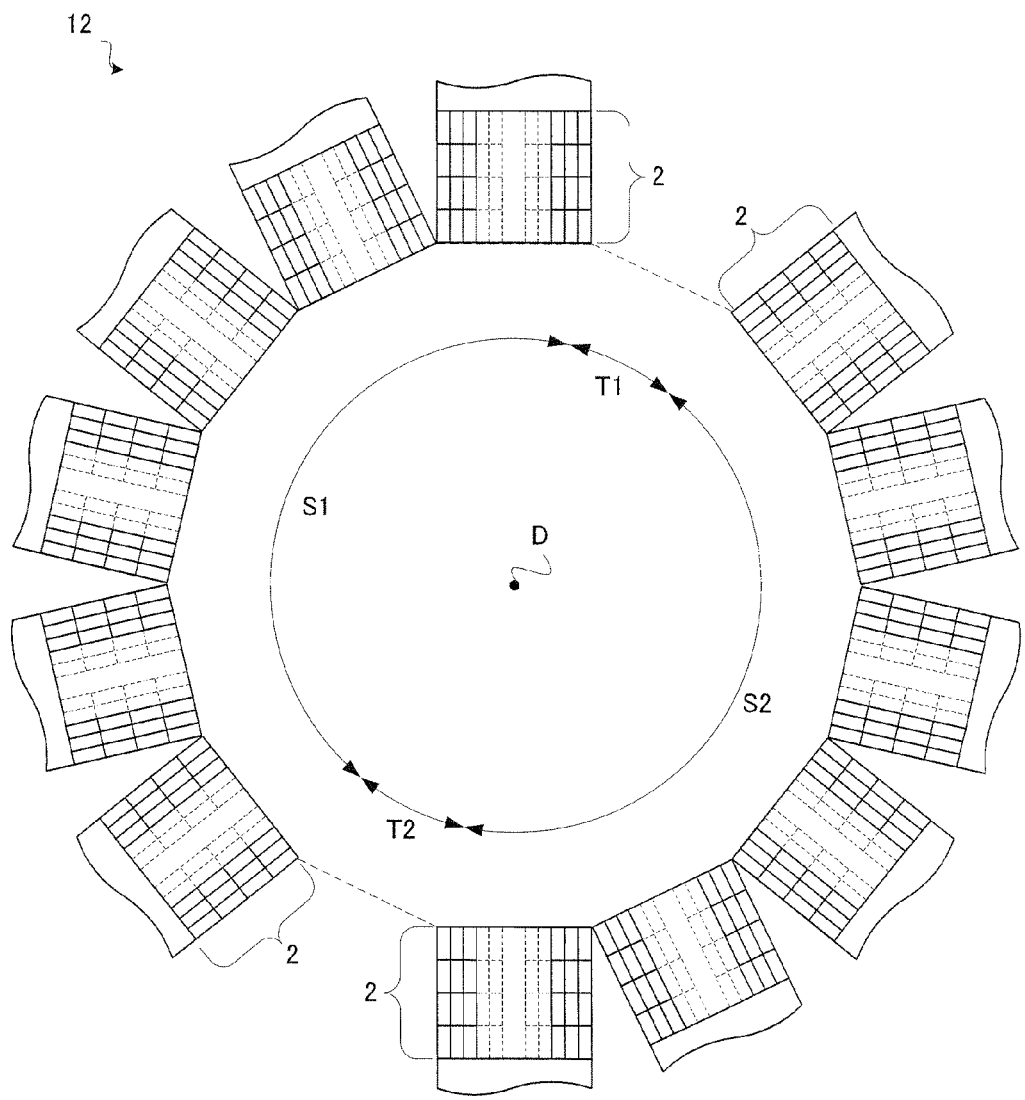
FIG. 20 is a plan view showing a configuration of a detector ring according to one modification of this invention.
Figure 22:
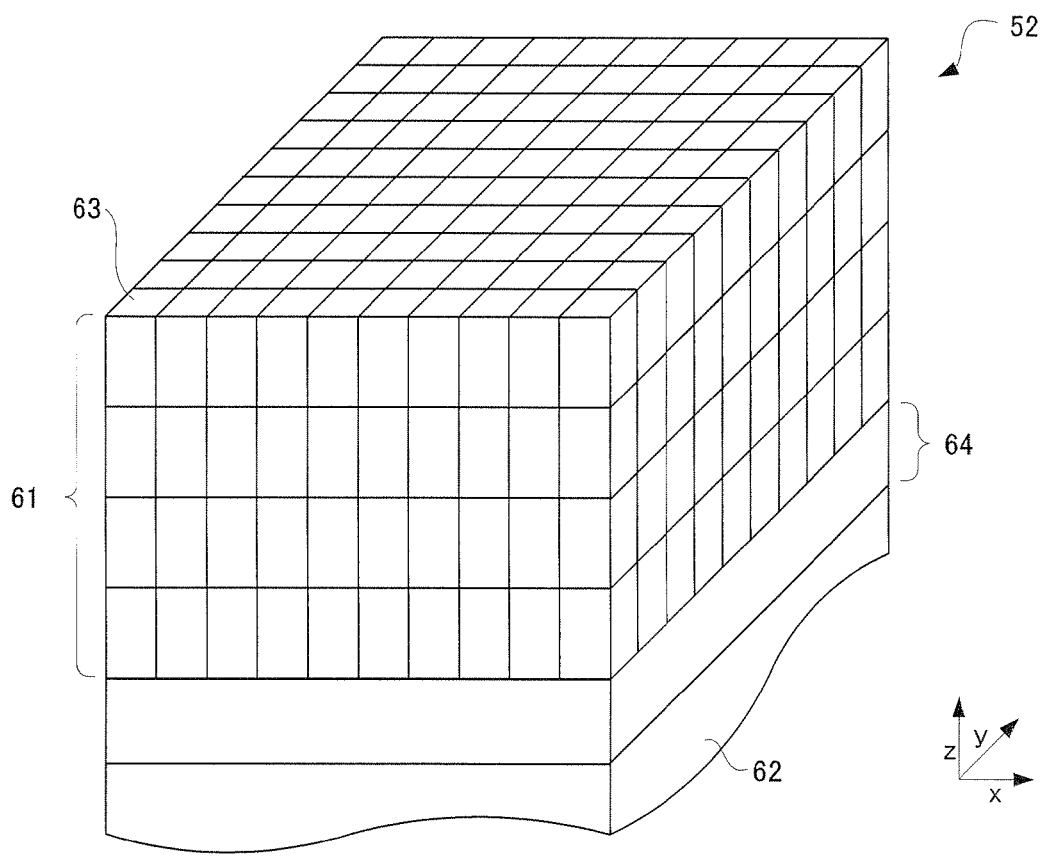
FIG. 22 is a perspective view showing the configuration of the conventional radiation tomography apparatus.

(6) In each of the foregoing embodiments, the detector ring has a single fracture portion T. This invention is not limited to the embodiments. As shown in FIG. 20, the detector ring has two or more fracture portions T 1 and T2 and two or more array portions S1 and S2 spaced away from each other. Such configuration is adaptable to a PET device for urinary-organs inspections.

(7) The fracture portion T is provided in each of the foregoing embodiments for a given purpose. This invention is not limited to the embodiments. That is, this invention is adaptable when the radiation detector 1 is out of order.

[Industrial Utility]

As described above, this invention is suitable for radiation tomography apparatus for use in medical fields.

The invention claimed is:

1. Radiation tomography apparatus comprising:
   a detector ring having radiation detecting elements for detecting radiation arranged in an arc shape;
   a coincidence device for counting a number of coincident events as a frequency where a first radiation detecting element and a second radiation detecting element coincidently detect radiation;
   a position specifying device for outputting positional information as a line connecting the first radiation detecting element and the second radiation detecting element; and
   a correlated data storing device for storing correlated data having the number of coincident events and corresponding positional information correlated therewith,
   the detector ring having an array portion where radiation detecting elements for detecting radiation are arranged and a fracture portion where no radiation detecting element is arranged,
   the apparatus further comprising:
   a correlated data complementation device for complementing correlated data on the fracture portion by calculating the number of coincident events and positional information corresponding thereto based on the correlated data under assumption that the first radiation detecting element is in the fracture portion for storing the number of coincident events and the positional information to the correlated data complementation device in addition;
   a detection efficiency acquisition device for acquiring a radiation detection efficiency in each radiation detecting element arranged in the detector ring by use of the correlated data and the correlated data through complementation; and
   a correction device for correcting a radiological image in accordance with the radiation detection efficiency.

2. The radiation tomography apparatus according to claim 1, wherein
   the correlated data complementation device duplicates the correlated data stored with the correlated data storing device and assumes that the duplication is counted in the fracture portion, thereby determining and complementing the number of coincident events and the positional information corresponding thereto under assumption that the first radiation detecting element is in the fracture portion.

3. The radiation tomography apparatus according to claim 2, wherein
   the correlated data complementation device performs complementation of the number of coincident events and the positional information corresponding thereto in the fracture portion by virtually rotating the first and second radiation detecting elements while maintaining a relative position therebetween to assume that the first radiation detecting element is in the fracture portion.

4. The radiation tomography apparatus according to claim 1, wherein
   the correlated data complementation device complements the number of coincident events under assumption that the first radiation detecting element is in the fracture portion through average of the two or more numbers of coincident events and assumption of the average to be counted in the fracture portion.

5. The radiation tomography apparatus according to claim 4, wherein
   the correlated data complementation device performs complementation of the number of coincident events in the fracture portion by virtually rotating the first and second radiation detecting elements while the relative position therebetween is maintained, collecting a pair of radiation detecting elements of rotational symmetry as a pair of radiation detecting elements having rotational symmetry in positional relationship of the first and second radiation detecting elements for averaging a number of coincident events corresponding to the pair of radiation detecting elements of rotational symmetry, and setting the average thereof to be the number of coincident events under assumption that the first radiation detecting element is in the fracture portion.

6. The radiation tomography apparatus according to claim 1, wherein
   the correlated data complementation device has a function to complement the number of coincident events assumed to be counted in the fracture portion by determining the number of coincident events acquired from the radiation detecting elements constituting the detector ring,
   the detection efficiency acquisition device once sets a detection efficiency of the radiation detecting elements arranged in the array portion to be a predetermined value, and sets a detection efficiency of the radiation detecting elements assumed to be in the fracture portion to be a predetermined value for calculating a detection efficiency of the radiation detecting elements based on the number of coincident events and the number of coincident events assumed to be counted in the fracture portion, and
   the detector efficiency acquisition device complements again a product of the number of coincident events assumed to be counted in the fracture portion and a renewed number of coincident events based on the acquired detection efficiency of the radiation detecting elements and the detection efficiency of the radiation element assumed to be in the fracture portion, thereby acquiring again the deletion efficiency of the radiation detecting elements arranged in the array portion, the detection efficiency of the radiation detecting elements assumed to be in the fracture portion being constant at a predetermined value.

7. The radiation tomography apparatus according to claim 6, wherein
the correlated data complementation device sets an average of the number of coincident events acquired through averaging the number of coincident events acquired from the radiation detecting elements constituting the detector ring to be the number of coincident events assumed to be counted in the fracture portion.

8. The radiation tomography apparatus according to claims 1, wherein
the radiation detecting elements are arranged at least in an arc shape along a circle or polygon to form a unit detector ring having the radiation detecting elements arranged in a row, and the two or more unit detector rings are stacked to form the detector ring.

9. The radiation tomography apparatus according to claim 1, wherein
the detector ring has two or more fracture portions spaced away from each other.

10. The radiation tomography apparatus according to claim 2, wherein
the radiation detecting elements are arranged at least in an arc shape along a circle or polygon to form a unit detector ring having the radiation detecting elements arranged in a row, and the two or more unit detector rings are stacked to form the detector ring.

11. The radiation tomography apparatus according to claim 3, wherein
the radiation detecting elements are arranged at least in an arc shape along a circle or polygon to form a unit detector ring having the radiation detecting elements arranged in a row, and the two or more unit detector rings are stacked to form the detector ring.

12. The radiation tomography apparatus according to claim 4, wherein
the radiation detecting elements are arranged at least in an arc shape along a circle or polygon to form a unit detector ring having the radiation detecting elements arranged in a row, and the two or more unit detector rings are stacked to form the detector ring.

13. The radiation tomography apparatus according to claim 5, wherein
the radiation detecting elements are arranged at least in an arc shape along a circle or polygon to form a unit detector ring having the radiation detecting elements arranged in a row, and the two or more unit detector rings are stacked to form the detector ring.

14. The radiation tomography apparatus according to claim 2, wherein the detector ring has two or more fracture portions spaced away from each other.

15. The radiation tomography apparatus according to claim 3, wherein the detector ring has two or more fracture portions spaced away from each other.

16. The radiation tomography apparatus according to claim 4, wherein the detector ring has two or more fracture portions spaced away from each other.

17. The radiation tomography apparatus according to claim 5, wherein the detector ring has two or more fracture portions spaced away from each other.

18. The radiation tomography apparatus according to claim 6, wherein the detector ring has two or more fracture portions spaced away from each other.

19. The radiation tomography apparatus according to claim 2, wherein
the correlated data complementation device has a function to complement the number of coincident events assumed to be counted in the fracture portion by determining the number of coincident events acquired from the radiation detecting elements constituting the detector ring,
the detection efficiency acquisition device once sets a detection efficiency of the radiation detecting elements arranged in the array portion to be a predetermined value, and sets a detection efficiency of the radiation detecting elements assumed to be in the fracture portion to be a predetermined value for calculating a detection efficiency of the radiation detecting elements based on the number of coincident events and the number of coincident events assumed to be counted in the fracture portion, and
the detector efficiency acquisition device complements again a product of the number of coincident events assumed to be counted in the fracture portion and a renewed number of coincident events based on the acquired detection efficiency of the radiation detecting elements and the detection efficiency of the radiation element assumed to be in the fracture portion, thereby acquiring again the deletion efficiency of the radiation detecting elements arranged in the array portion, the detection efficiency of the radiation detecting elements assumed to be in the fracture portion being constant at a predetermined value.

20. The radiation tomography apparatus according to claim 3, wherein
the correlated data complementation device has a function to complement the number of coincident events assumed to be counted in the fracture portion by determining the number of coincident events acquired from the radiation detecting elements constituting the detector ring,
the detection efficiency acquisition device once sets a detection efficiency of the radiation detecting elements arranged in the array portion to be a predetermined value, and sets a detection efficiency of the radiation detecting elements assumed to be in the fracture portion to be a predetermined value for calculating a detection efficiency of the radiation detecting elements based on the number of coincident events and the number of coincident events assumed to be counted in the fracture portion, and
the detector efficiency acquisition device complements again a product of the number of coincident events assumed to be counted in the fracture portion and a renewed number of coincident events based on the acquired detection efficiency of the radiation detecting elements and the detection efficiency of the radiation element assumed to be in the fracture portion, thereby acquiring again the deletion efficiency of the radiation detecting elements arranged in the array portion, the detection efficiency of the radiation detecting elements assumed to be in the fracture portion being constant at a predetermined value.

* * * * *